United States Patent
Retterath et al.

(10) Patent No.: US 7,411,681 B2
(45) Date of Patent: *Aug. 12, 2008

(54) SYSTEM FOR AUTOMATED DETERMINATION OF RETROREFLECTIVITY OF ROAD SIGNS AND OTHER REFLECTIVE OBJECTS

(75) Inventors: James E. Retterath, Excelsior, MN (US); Robert A. Laumeyer, Minneapolis, MN (US)

(73) Assignee: Facet Technology Corporation, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/702,421

(22) Filed: Feb. 5, 2007

(65) Prior Publication Data

US 2007/0216904 A1 Sep. 20, 2007

Related U.S. Application Data

(63) Continuation of application No. 11/381,503, filed on May 3, 2006, now Pat. No. 7,173,707, which is a continuation of application No. 10/736,454, filed on Dec. 15, 2003, now Pat. No. 7,043,057, which is a continuation of application No. 09/918,375, filed on Jul. 30, 2001, now Pat. No. 6,674,878.

(51) Int. Cl.
G01N 21/55 (2006.01)

(52) U.S. Cl. .................................................... 356/445

(58) Field of Classification Search .................. 356/121, 356/445–448, 508, 237.3, 455; 359/529, 359/627

See application file for complete search history.

(56) References Cited

U.S. PATENT DOCUMENTS

| | | | | |
|---|---|---|---|---|
| 5,050,327 A | * | 9/1991 | Woltman | 40/582 |
| 5,530,549 A | * | 6/1996 | Brown | 356/622 |
| 6,048,069 A | * | 4/2000 | Nagaoka et al. | 359/529 |
| 6,212,480 B1 | | 4/2001 | Dunne | |
| 6,266,442 B1 | | 7/2001 | Laumeyer et al. | |
| 6,674,878 B2 | * | 1/2004 | Retterath et al. | 382/104 |
| 7,043,057 B2 | | 5/2006 | Retterath et al. | |
| 2004/0156531 A1 | * | 8/2004 | Retterath et al. | 382/104 |
| 2006/0262312 A1 | * | 11/2006 | Retterath et al. | 356/445 |

* cited by examiner

Primary Examiner—Tarifur R. Chowdhury
Assistant Examiner—Isiaka O Akanbi
(74) Attorney, Agent, or Firm—Patterson, Thuente, Skaar & Christensen, P.A.

(57) ABSTRACT

A system for the automated determination of retroreflectivity values for reflective surfaces disposed along a roadway repeatedly illuminates an area along the roadway that includes at least one reflective surface using a strobing light source. Multiple light intensity values are measured over a field of view which includes at least a portion of the area illuminated by the light source. A computer processing system is used to identifying a portion of the light intensity values associated with a reflective surface and analyze the portion of the light intensity values to determine at least one retroreflectivity value for that reflective surface.

1 Claim, 16 Drawing Sheets

SYSTEM FOR AUTOMATED DETERMINATION OF RETROREFLECTIVITY OF ROAD SIGNS AND OTHER REFLECTIVE OBJECTS

RELATED APPLICATIONS

This application is a continuation of application Ser. No. 11/381,503 filed May 3, 2006, now U.S. Pat. No. 7,173,707 issued Feb. 3, 2007, which in turn is a continuation of application Ser. No. 10/736,454 filed Dec. 15, 2003, now U.S. Pat. No. 7,043,057 issued May 9, 2006, which in turn is a continuation of Ser. No. 09/918,375 filed Jul. 30, 2001 now U.S. Pat. No. 6,674,878 issued Jan. 6, 2004.

FIELD OF THE INVENTION

The present invention relates to the field of automated electronic measurement and object identification systems. More particularly, the present invention is directed to methods and an apparatus for the automated determination of certain characteristics of desired reflective objects (such as road signs) and classifying the reflective objects as to the level of retroreflectivity.

BACKGROUND OF THE INVENTION

Safe motor vehicle travel during low light and nighttime conditions requires that directional, regulatory and cautionary information displayed upon road signs and markers be clearly visible to a vehicle operator traveling at a reasonable velocity down a roadway. Various kinds of reflective sheeting, decals and paints are used on road signs and markers to enhance the readability and perception of information displayed during low light and nighttime conditions. Unfortunately, the effectiveness of these reflective materials tends to deteriorate over time.

Adequate nighttime and low light visibility of roadway signs by vehicle operators is best associated and most impacted with the retroreflectance properties of the individual signs. Retroreflectivity (defined as the ability of a material to reflect incident light back towards its source), specified in candelas per lux per square meter ($cd/lux/m^2$), is an important characteristic utilized by transportation agencies to assess the nighttime visibility of road signs.

Generally, highway and street maintenance departments do not systematically evaluate the deterioration of the reflective materials used on road signs and markers. If inspections of road signs or markers are performed, they are typically accomplished by having inspectors manually position a handheld retroreflectometer directly on the surface of a sign in order to determine a retroreflectivity value for that sign. When there are a large number of road signs or markers (sometimes referred to as traffic control devices or TCDs) in a given jurisdiction, the task of manually inspecting all of these road signs and markers can be time consuming and expensive.

One technique for determining retroreflectivity which does not require that a retroreflectometer be placed directly on a sign is described in U.S. Pat. No. 6,212,480 entitled, "APPARATUS AND METHOD FOR DETERMINING PRECISION REFLECTIVITY OF HIGHWAY SIGNS AND OTHER REFLECTIVE OBJECTS UTILIZING AN OPTICAL RANGE FINDER INSTRUMENT," issued Apr. 3, 2001 to Dunne. The Dunne patent relates to a device commercialized by the assignee thereof and marketed as the "Impulse RM" retroreflectometer by Laser Technology, Inc., of Englewood, Colo., USA. In use, handheld devices fabricated according to the Dunne patent are manually directed toward, or precisely at, a target object and then manually "fired." Once fired, the handheld device bounces a laser off the target object and measures the reflected laser energy that is then used to determine a retroreflectivity.

There are several drawbacks of the handheld laser arrangement described by the Dunne patent. The handheld device can only measure a single color at a time and can only measure one object at a time. The determination of retroreflectivity for a given object is valid only for the actual location, or discrete measurement point, along the roadway at which the measurement was made by the human operator. In order to validate a measurement made by such devices, the device must be taken back to the precise location in the field where an original measurement occurred for a valid comparison measurement to be made.

Another technique established for determining the nighttime visibility of signs has been introduced by the Federal Highway Administration (FHWA). The Sign Management and Retroreflectivity Tracking System (SMARTS) is a vehicle that contains one high intensity flash source (similar to the Honeywell StrobeGuard™ SG-60 device), one color camera, two black and white cameras, and a range-sensing device. The SMARTS vehicle requires two people for proper operation—one driver and one system operator to point the device at the target sign and arm the system. The SMARTS travels down the road, and the system operator "locks on" to a sign up ahead by rotating the camera and light assembly to point at the sign. At a distance of 60 meters, the system triggers the flash source to illuminate the sign surface, an image of which is captured by one of the black and white cameras. A histogram is produced of the sign's legend and background that is then used to calculate retroreflectivity. A GPS system stores the location of the vehicle along with the calculated retroreflectivity in a computer database.

Like the handheld laser device of the Dunne patent, the SMARTS device can only determine retroreflectivity for one sign at a time and can only determine retroreflectivity for the discrete point on the roadway 60 meters from the sign. Two people are required to operate the vehicle and measurement system. The SMARTS vehicle cannot make retroreflectivity determinations for signs on both sides of the roadway in a single pass over the roadway and does not produce nighttime sign visibility information for lanes on the roadway not traveled by the vehicle. Because the system operator in the SMARTS vehicle must locate and track signs to be measured while the vehicle is in motion, a high level of operational skill is required and the likelihood that a sign will be missed is significant.

There are an estimated 58 million individual TCDs that must be monitored and maintained in the United States and new TCD installations increase this number daily. For the reasons that have been described, the existing techniques for determining retroreflectivity do not lend themselves to increasing processing throughput so as to more easily manage the monitoring and maintenance of these TCDs. So called automated data collection systems often require that normal traffic be stopped during data collection because either the acquisition vehicle moved very slowly or because the acquisition vehicle had to come to a full stop before recording data about the roadside scene. Furthermore, a human operator is required to point one or more measurement devices at a sign of interest, perform data collection for that particular sign and then set up the device for another particular sign of interest. With such a large number of TCDs that must be monitored, it would be desirable to provide an automated system for determining the retroreflectivity of road signs and markers that addresses these and other shortcomings of the existing techniques to enable a higher processing throughput of an automated determination of the retroreflectivity of road signs and markers.

SUMMARY OF THE INVENTION

The present invention provides a system for the automated determination of retroreflectivity values for reflective surfaces disposed along a roadway. An area along the roadway that includes at least one reflective surface is repeatedly illuminated by a light source and multiple light intensity values are measured over a field of view which includes at least a portion of the area illuminated by the light source. A computer processing system is used to identify a portion of the light intensity values associated with a reflective surface and analyze the portion of the light intensity values to determine at least one retroreflectivity value for that reflective surface. Preferably, color images of the area and locational information are also generated by the system and are used together with a characterization profile of the light source to enhance the accuracy of the determination of retroreflectivity values. In one embodiment, a three-dimensional overlay of retroreflectivity values for the roadway is generated and can be manipulated to display retroreflectivity values of a reflective surface at any desired point along the roadway. In another embodiment, a virtual drive-through along a roadway is simulated using a plurality of retroreflectivity values to simulate reflections from each reflective surface disposed along the roadway during the virtual drive-through.

In contrast to the existing techniques for determining retroreflectivity that require an operator to target individual signs from a known distance, the present invention can determine retroreflectivity without targeting individual signs and can calculate retroreflectivity values at any desired point along a roadway. To overcome the limitations imposed by the existing techniques, the present invention employs several enhancements that are designed to improve the accuracy of evaluating intensity measurements made over a view where the reflective surfaces are not individually targeted and, therefore, neither the distance to the reflective surface or the normal vector to the reflective surface are known.

In a method in accordance with the present invention, retroreflectivity values for reflective surfaces disposed along a roadway are determined in an automated manner. A light source is strobed as the light source is traversed along the roadway to illuminate an area that includes at least one reflective surface. A plurality of light intensity measurements are collected using at least one intensity sensor directed to cover a field of view which includes at least a portion of the area illuminated by the light source. A computer processing system is then used to identify a portion of at least one light intensity measurement associated with one of the at least one reflective surfaces and analyze the portion of the at least one light intensity measurement to determine at least one retroreflectivity value for that reflective surface.

In a preferred embodiment of the method in accordance with the present invention, a characterization profile for the light source is created for this method. The characterization profile includes an array of known luminance values of reflections of the light source. The characterization profile for the light source is then utilized as part of determining the at least one retroreflectivity value for that reflective surface. Preferably, the array of known luminance values of reflection comprises reflected intensity values for the light source over a range of colors and reflected intensity values over a range of relative angles between the light source and the reflective surface. In one embodiment, a plurality of color images are captured using at least one color camera directed to cover a field of view which includes at least a portion of the area illuminated by the light source. The range of colors of the characterization profile for the light source and the plurality of color images are then used as part of determining the at least one retroreflectivity value for that reflective surface. In another embodiment, locational information is obtained for each of the plurality of light intensity measurements and used to determine a coordinate location for each reflective surface. The range of relative angles of the characterization profile for the light source and the coordinate location are then used as part of determining the at least one retroreflectivity value for that reflective surface. Preferably, a characterization profile of the light intensity sensor is also utilized to further enhance the accuracy of the system. The characterization profile for the intensity sensor preferably includes an array of intensity values of reflections as measured by the intensity sensor in response to a known light source.

A system for acquiring information to assess reflective surfaces disposed along a roadway in accordance with the present invention includes a vehicle and a computer processing system. The vehicle includes at least one high output light source, at least one intensity sensor, at least one color camera, a positioning system, and a control system. The control system is operably connected to the light source, intensity sensor, color camera and positioning system such that the intensity sensor, color camera and positioning system record information associated with an area that includes at least one reflective surface as the vehicle traverses along the roadway in response to repeated illumination of the area by the light source. The computer processor, which may reside within the vehicle or may be located separate from the vehicle, utilizes the recorded information to determine at least one retroreflectivity value for the at least one reflective surface.

In a preferred embodiment of the system, the vehicle further includes a laser scanning system that records distance information including at least a distance between the vehicle and each of the at least one reflective surfaces. The computer processing system utilizes the distance information generated by the laser scanning system to determine at least a normal vector for a face of the reflective surface. Preferably, the high output light source comprises at least two strobe lights arranged to alternatively illuminate the area at an effective strobe rate of at least one flash per second. Preferably, the intensity sensor comprises a black and white camera and the color camera comprises a pair of digital color cameras mounted on the vehicle to generate stereoscopic images of the area. The positioning system is preferably a global positioning system supplemented with an inertial navigation system. In the embodiment in which at least a portion of the computer processing system resides within the acquisition vehicle, at least a portion of the control system is preferably implemented using the computer processing system and a master clock supplied to all of the remaining components of the system to synchronize the system.

In another embodiment of the present invention, a method for displaying and manipulating retroreflectivity data for a reflective surface disposed along a roadway is provided. A plurality of retroreflectivity values for the reflective surface are determined, preferably using the method and system as described. A three-dimensional representation of retroreflectivity values of the reflective surface is generated and the three-dimensional representation of retroreflectivity values is displayed, preferably as an overlay over a depiction of a roadway. A simulation of the interaction of a vehicle operator/observer is accomplished by generating a simulated vehicle light source and a vehicle operator/observer pair and, for different locations of the simulated vehicle light source and said vehicle operator/observer pair, generating a simulated vehicle operator/observer observation angle and a simulated view of the vehicle pathway which includes the reflective surface. The simulation allows for simulating a changing magnitude of ambient lighting from a first value to a second value, or simulating a change of at least one characteristic of the depiction of the roadway. A corresponding change in the three-dimensional representation of retroreflectivity values as a result is determined and also simulated on the display. In one embodiment, the simulation is used to generate a new three-dimensional depiction of the reflective surface according to a predictive aging model which includes a gradual degradation of the reflective surface over time. The reflective surface can then be represented and simulated as if the reflective surface exhibited such a gradual degradation in the three-dimensional depiction.

In another embodiment, a method for simulating a virtual drive-through of a roadway that includes at least one reflective surface disposed along the roadway is provided. A plurality of retroreflectivity values are determined for each reflective surface. A virtual drive-through along the roadway is simulated using the plurality of retroreflectivity values to simulate reflections from each reflective surface disposed along the roadway during the virtual drive-through. Preferably, the virtual drive through allows for a simulation of a change of at least one characteristic of the depiction of the roadway, such that a corresponding change in the reflections from each reflective surface is determined and simulated. Preferably, the virtual drive-through simulates at least one vehicle having a light source and observer pair. In this embodiment, the virtual drive-through allows for a simulation of a change of at least one characteristic of the vehicle or light source and observer pair, such that a corresponding change in the reflections from each reflective surface is determined and simulated.

DETAILED DESCRIPTION OF THE PREFERRED EMBODIMENTS

Figure 1:
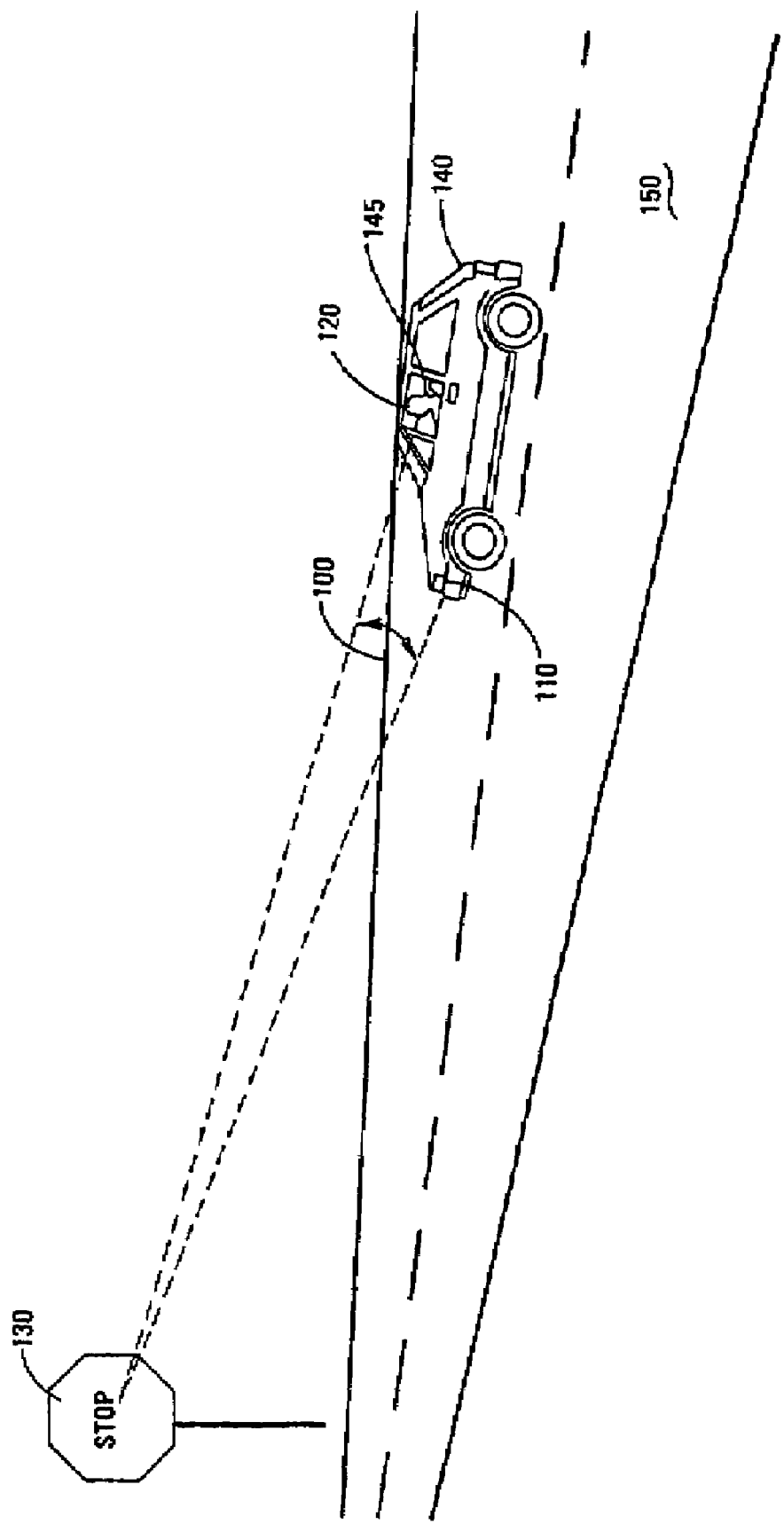
FIG. 1 depicts the concept of observation angle (i.e., angle between incident light from a light source and an human observer [or light sensor], of the light as reflected from the face of a reflective asset) in the context of a conventional passenger vehicle traversing a vehicle pathway and where light from the vehicle reflects from a stop sign to the vehicle operator (shown in ghost).

Retroreflectivity, designated as "$R_A$" generally (and from time to time in this disclosure), varies according to two key parameters: observation angle and entrance angle. Observation angle 100 (See FIG. 1) is the angular displacement between a light source 110 and a light sensor 120, as measured from an object face surface 130. In the case of a vehicle 140 driven by vehicle operator 145 moving along a highway 150, observation angle 100 is defined by the distance of the vehicle 140 from a sign face surface 130, the placement of the light source (headlights) 110 on the vehicle 140, and the position of the light sensor (eyes of the vehicle operator) 120 of the vehicle 140.

Figure 2:
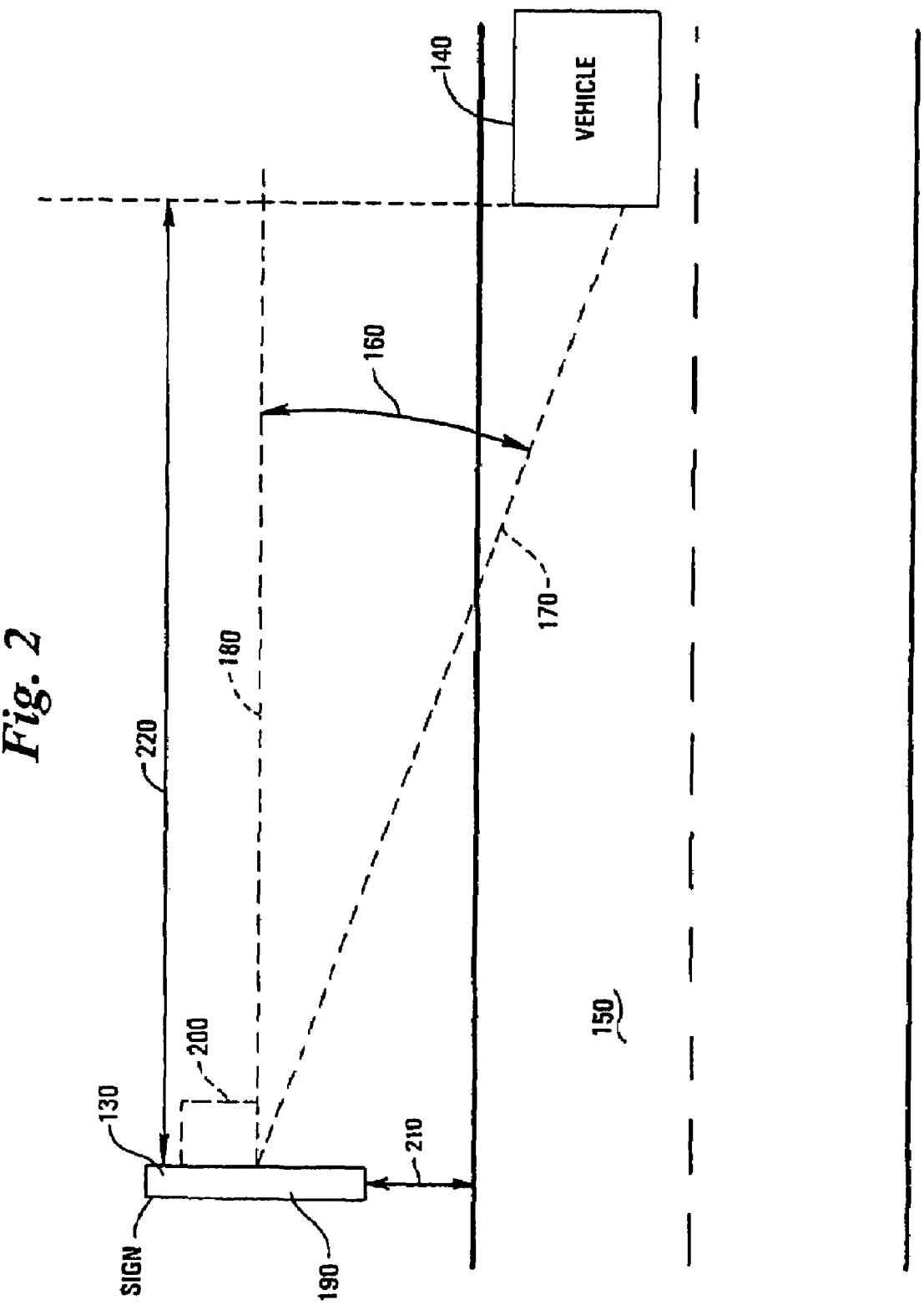
FIG. 2 depicts the concept of entrance angle (i.e., angle between incident light from a light source mounted to a vehicle and a normal vector relative to the substantially flat face of a reflective surface disposed adjacent a vehicle pathway).

Entrance angle 160 (See FIG. 2) is defined as the angular displacement of the incident light 170 relative to the normal vector 180 from the object face surface 130. Entrance angles are impacted by the angular position 200 of a sign 190 relative to the highway 150, the sign 190 lateral distance 210 from the highway 150, and the distance 220 of the vehicle 140 from the sign 190. The inventors hereof are believed to be the first persons to successfully decrease the complexity and increase the efficiency of determination of $R_A$ in the field.

The method of automatic determination of $R_A$ (See FIGS. 3 and 4) preferably utilizes a plurality of subsystems located on/in a capture vehicle 225. These subsystems include a light intensity measurement system 230, a vehicle positioning system 240, a color image capture system 250 and a data recording system 260. The light intensity measurement system 230 preferably includes a high output light source 270, a light intensity sensor 280 and an intensity measurement system control 290. A plurality of intensity measurements 300 are generated by the intensity measurement system 230 in response to the repeated strobing of the high output light source 270. The vehicle positioning system 240 preferably includes a GPS receiver 310, an inertial navigation system 320, a distance measuring instrument 330 and a master clock 340. A position measurement 350 is generated by the vehicle positioning system 240. The color image capture system 250 preferably includes a stereoscopic camera pair 360, iris controls 370 and image capture control 380. The image capture system 250 generates a digital imagery stream 390.

Figure 5:
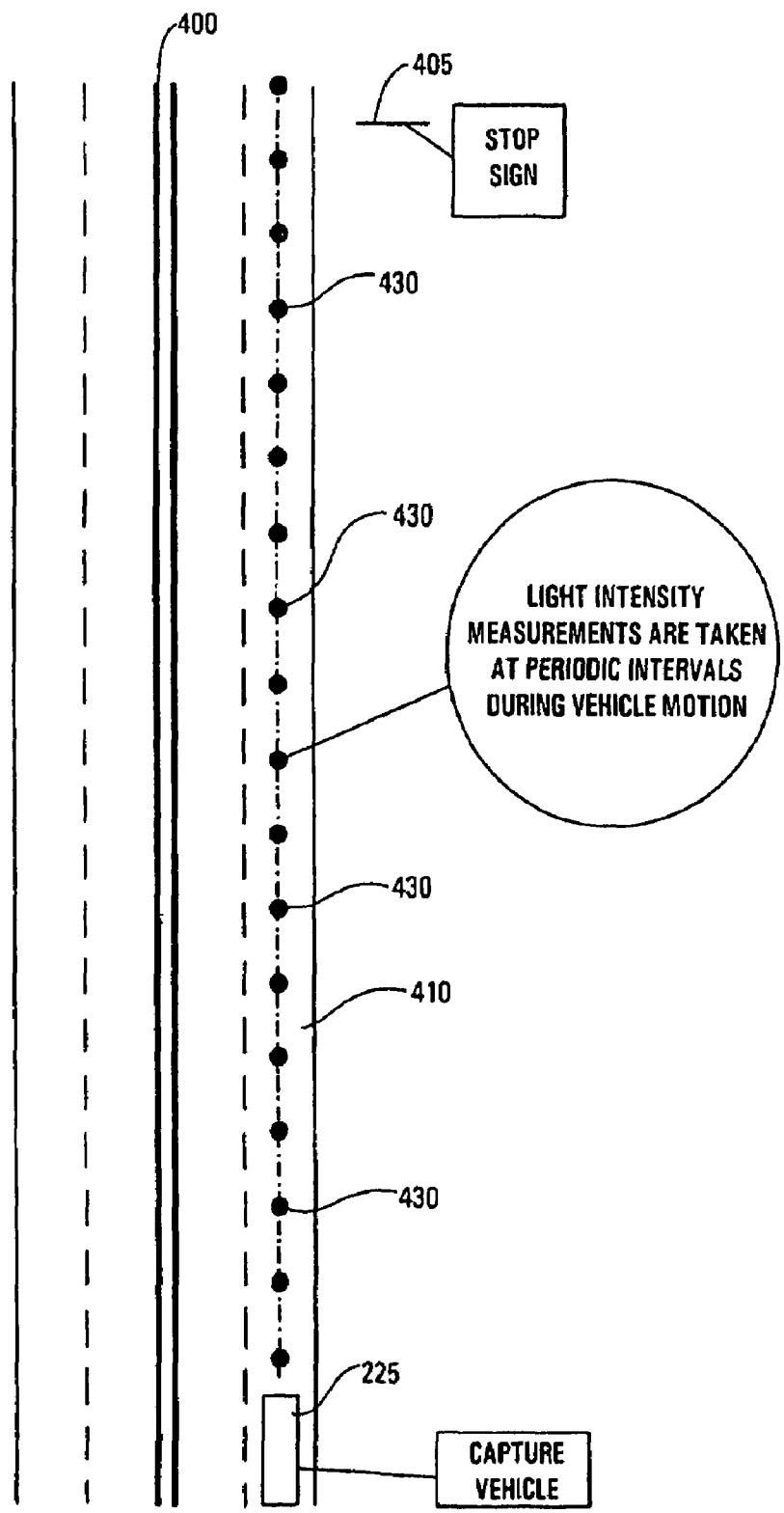
FIG. 5 is a plan view of a divided multi-lane vehicle pathway and depicts how periodic light intensity measurements may be made as a vehicle traverses the vehicle pathway over time and the discrete locations where such periodic light intensity measurements are performed by a data acquisition vehicle operating in accordance with the present invention.
Figure 6:
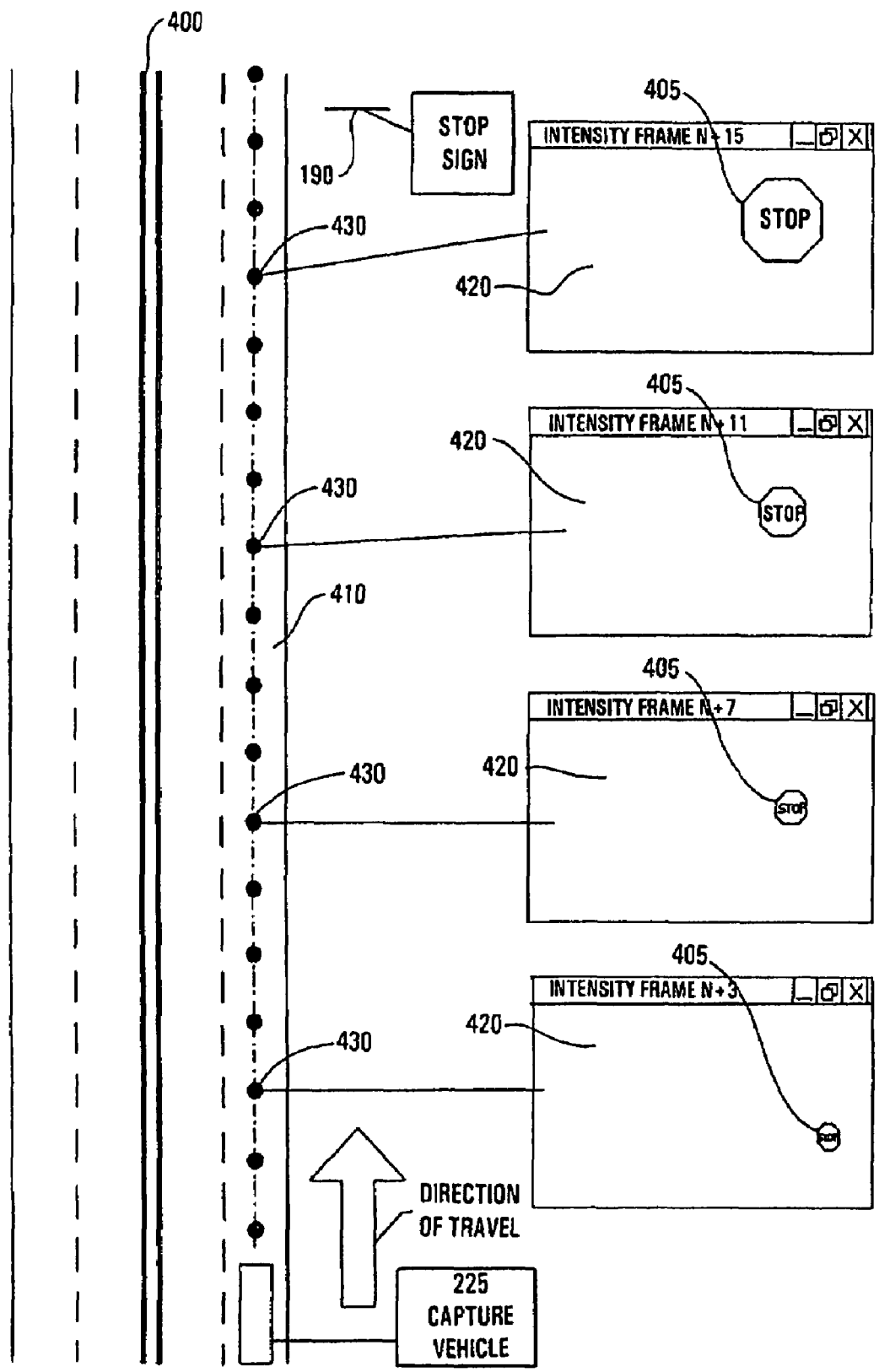
FIG. 6 depicts four digital frames of data as captured by the intensity sensor at various discrete locations along the vehicle pathway depicted in FIG. 5.

The data required for the automated determination of $R_A$ is accumulated while traversing a highway 150 with the capture vehicle 225 (See FIGS. 5 and 6). The capture vehicle 225 is shown on a 4-lane divided highway 400 with the capture vehicle 225 located in a proximate lane 410 to the stop sign 190. Preferably, a series of reflected light intensity frames 420 are generated at a constant measurement interval 430 as the capture vehicle travels along the highway 150.

Characterization of sign 190 $R_A$ preferably utilizes the data recording system 260 to create a single tagged video stream 440 from the reflected light intensity frames 420, position measurements 350 and digital imagery 390 for each capture event 430 (See FIGS. 3, 5, 6, 7 and 8). A computer processor 450 identifies an object of interest 460 in a portion of the intensity frame 420 and determines the object of interest attributes 465 associated with that object of interest. Preferably, the object of interests are identified from the digital imagery stream 390 generated by the color image capture system 250 in the manner as taught by U.S. Pat. No. 6,266,442. Alternatively, other techniques known in the art for isolating an object of interest in a videostream can be used. Preferably, the computer processor 450 correlates the portion of an image frame of the digital imagery stream 290 with a similar portion of the intensity frame 420 containing the object of interest 460.

For each object of interest 460, a background intensity measurement 470 and a foreground intensity measurement 480 is generated. Using an intensity algorithm 490, a light intensity sensor characterization 275 and a look-up-table 475, the computer processor 450 determines a background luminance value 500 and a foreground luminance value 510. Based on the background luminance value 500, the foreground luminance value 510, a characterization of light source wavelength 540, the background sheeting color 505 and the foreground sheeting color 506 the computer processor 450 characterizes a background $R_A$ 520 and a foreground $R_A$ 530 which are preferably reported separately for that object of interest.

Figure 9:
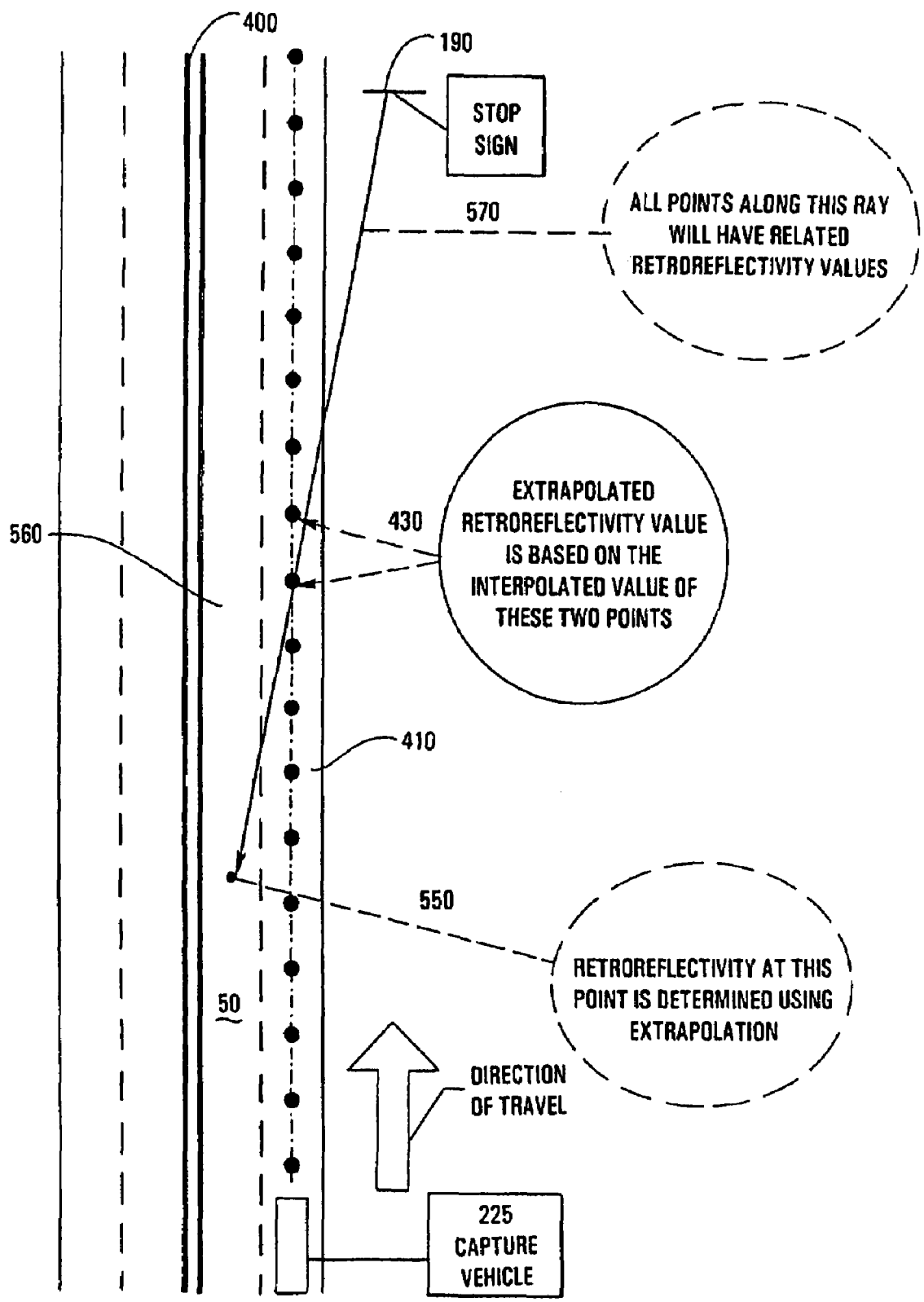
FIG. 9 depicts a preferred methodology for creating a three-dimensional retroreflectivity profile for all lanes and locations adjacent a vehicle pathway for a single reflective asset or sign which three-dimensional retroreflectivity profile is based upon a single pass of a data acquisition vehicle over the vehicle pathway.
Figure 10:
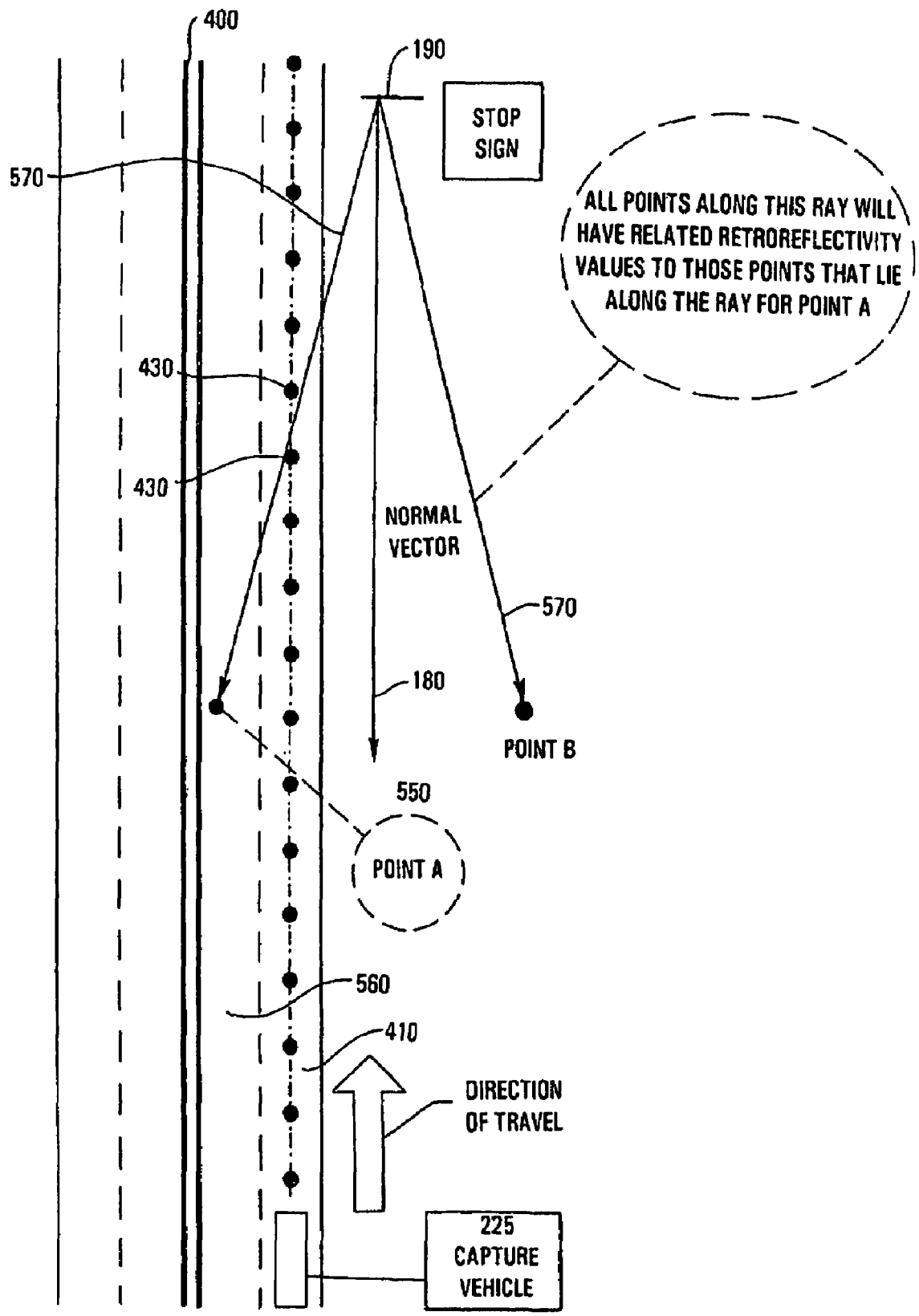
FIG. 10 illustrates the facts that the normal vector of a reflective asset and the sheeting type of such a reflective asset create symmetry that may be used to determine retroreflectivity values along all rays (or vectors) that have the same relative angle to the normal vector of the reflective asset.

The automated determination of multiple $R_A$ values for a given object of interest 460 allows for the extrapolation of $R_A$ values at an unmeasured viewing point 550 for an object of interest, such as a sign 190 (See FIGS. 9 and 10). In this example, the unmeasured viewing point resides in a nontraversed lane 560. The computer processor 450 defines an undetermined retroreflectivity ray 570 for unmeasured viewing point 550. Using interpolated values, the computer processor 450 determines an $R_A$ value for unmeasured viewing point 550 and any point located along undetermined retroreflectivity ray 570.

In one embodiment, the computer processor 450 can generate a simulated roadway 580 including roadway edges 585 and lane dividers 586 from information captured by the color imaging system 250 (See FIGS. 11, 12, 13, 14 and 15). The computer processor 450 then generates a three-dimensional sign $R_A$ profile 590 for either foreground $R_A$ 530 or background $R_A$ 520 to be overlayed on the simulated roadway 580. The computer processor 450, or any other computer processor accessing in a standalone end user mode accessing the retroreflectivity data, can manipulate the data such that additional simulations can be performed including a sheeting type improvement simulation 600, a sign profile rotation simulation 610 and a observation angle simulation 620.

Figure 16:
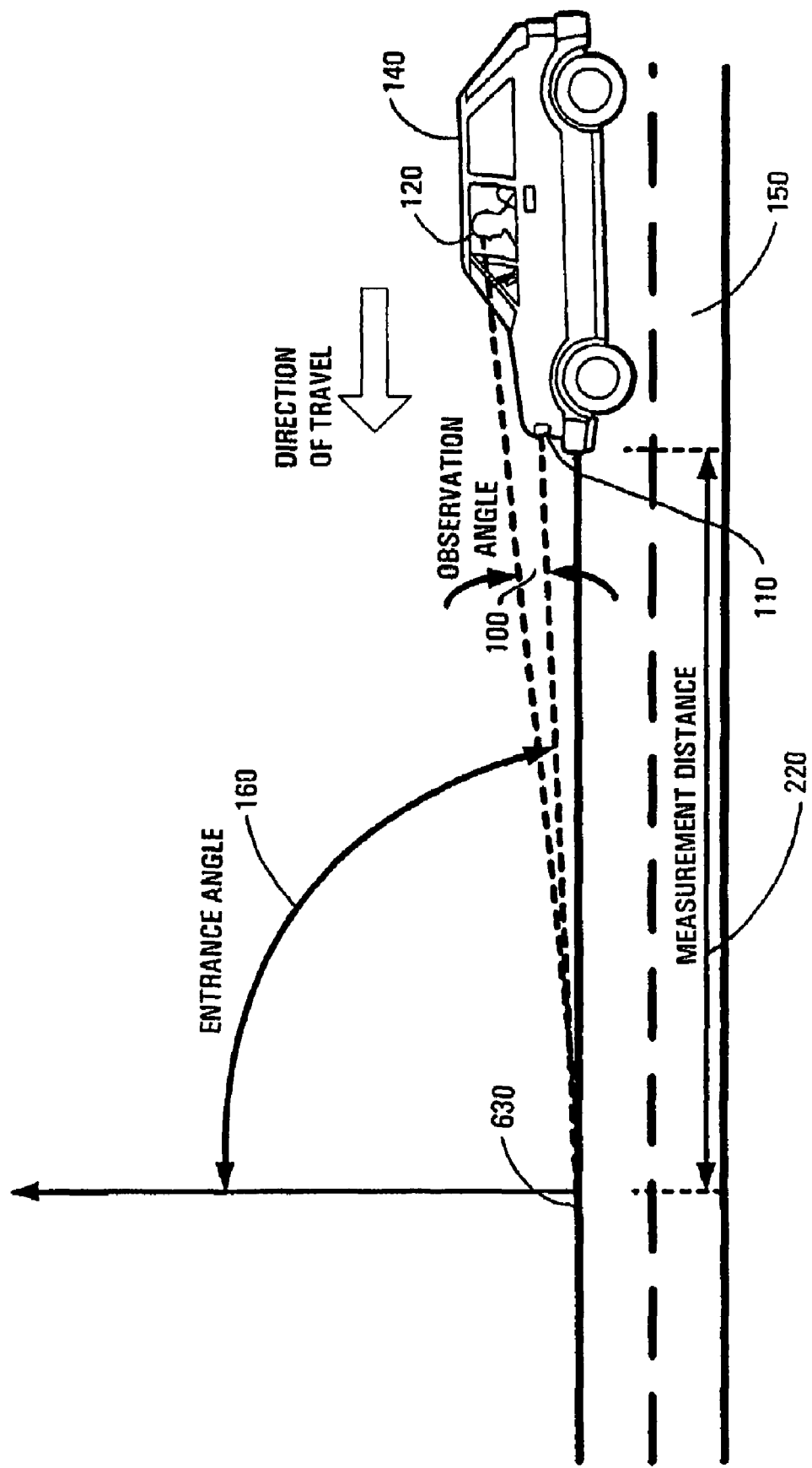
FIG. 16 depicts the geometry of entrance angle and observation angle for retroreflective pavement markings disposed upon a vehicle pathway.

An alternative embodiment of the present invention allows for the determination of retroreflectivity for pavement markings 630 (See FIG. 16). While the reflective surfaces of the present invention are described with respect to road signs and pavement markings along a roadway, it will be understood that the present invention is equally applicable to other reflective surfaces such as taillights or vehicle markings and to environments other than roadways such as airport runways, factories or the like.

Pursuant to the teaching of the present invention, a method and apparatus for determining retroreflectivity of relatively flat surface portions of objects disposed adjacent a highway 150 traversed by a vehicle 140 are taught, enabled and depicted. The present invention may be utilized to detect and determine a retroreflective surface of interest disposed in a scene of non-retroreflective surfaces. That is, at least one object face surface 130 which exhibits retroreflectivity over at least a relatively narrow conical volume of magnitude of several degrees from a normal vector 180 originating from said object face surface 130.

In accordance with the present invention, a determination of the retroreflectivity of objects adjacent a highway 150 preferably includes (i) providing position measurements 350 of a capture vehicle 225; (ii) precise position of the object of interest 460, or sign 190; (iii) intensity measurements 300 from a high output light source 270 and light intensity sensor 280 at measurement intervals 430 along said highway 150. Thus, a single-pass along the highway 150 by the capture vehicle 225 operating the light intensity measurement system 230, vehicle positioning system 240, image capture system 250 and data recording system 260 taught herein eliminates many shortcomings of the prior art and allows a single vehicle operator to conduct virtually continuous data measurement and acquisition of objects of interest 460 disposed adjacent a highway 150, at capture events 430 on said highway 150, without disrupting or interrupting other vehicle traffic traversing said highway 150.

Figure 3:
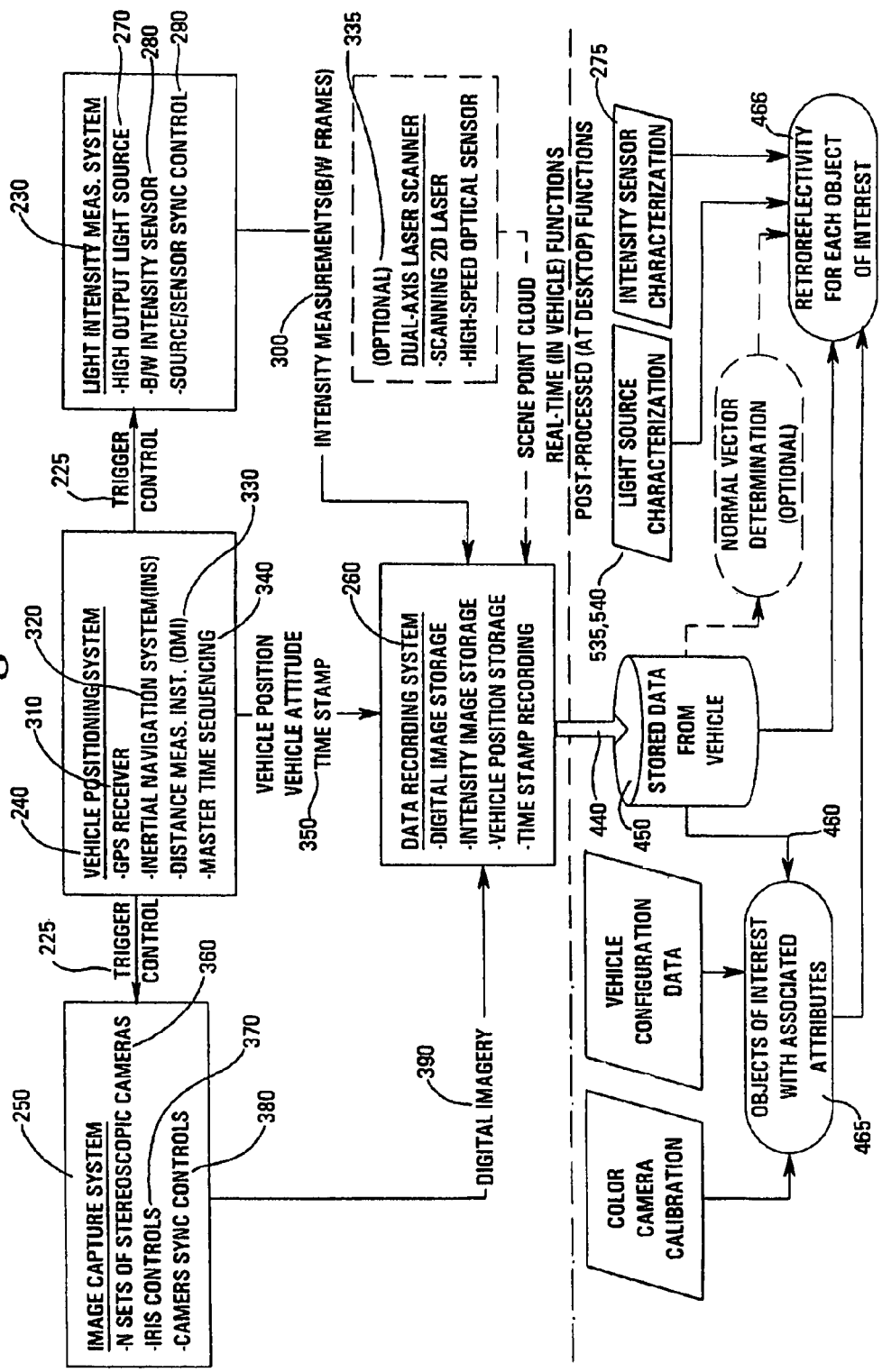
FIG. 3 depicts a block diagram of the systems, subsystems and processes for capturing and processing roadside information from a moving platform in order to compute retroreflectivity according to the teaching of the present invention wherein the arrows connecting the blocks of the diagram illustrate the connections between the systems and subsystems for computing $R_A$ for each reflective asset recorded by the system of the present invention.

FIG. 3 shows a block diagram of the on-board systems and the desktop systems required to record a tagged videostream 440 and create three-dimensional (3D) sign $R_A$ profiles 590 for various signs 190 along a highway 150. The vehicle positioning system 240 contains all of the equipment to precisely locate the capture vehicle 225. All location information is synchronized with a master clock 340, preferably associated with a computer processor 450, which allows other data types to be merged with the vehicle location information at later stages in the post-processing. All of the on-board systems utilize the same master clock 340 information, thus allowing any events (image capture system 250, intensity measurement 300, and trigger controls 227, 228) to be correlated to the precise vehicle location and attitude during real-time, near real-time, or post-processing of the data acquired by the capture vehicle 225.

The image capture system 250 consists of at least one set of stereoscopic cameras 360 that gather digital imagery along the highway 150. Each capture event is combined with time stamp information from the vehicle positioning system 240 which also provides trigger control 227 for the image capture system 250 and trigger control 228 for the light intensity measurement system 230. These images and associated time stamps are later combined with photogrammetry to create objects of interest 460 and their associated attributes 465.

The light intensity measurement system 230 preferably consists of at least one high output light source(s) 270 and the associated light intensity sensor(s) 280. The precise control for these items is contained within the light intensity measurement system 230, and master time sequencing instrument 340 information received from the vehicle positioning system 240 (or computer processor 450) is combined to create a tagged videostream 440 so precise vehicle information can be utilized during post-processing.

The data recording system 260 is constantly monitoring control information from the other three on-board systems and records the necessary information. No post-processing is performed in the data recording system 260. As computer power increases in the future, one skilled in the art could produce a system whereby most, if not all, of the post-processing functions were performed in the capture vehicle 225, perhaps even in real-time. The inventors can imagine several uses for the production of real-time information from the image capture system 250 in the future, but the cost of obtaining such information with today's computing power makes this option prohibitively expensive today.

The lower half of FIG. 3 shows the functional blocks for data post-processing. There are two main functions—the creation of objects of interest 460 and their associated attributes 465, and the determination of retroreflectivity for each object of interest 460. There are many methods for creating objects of interest 460 from digital imagery, a few of which are discussed in this disclosure. The specific steps required to compute $R_A$ are outlined in the discussion below.

Figure 4:
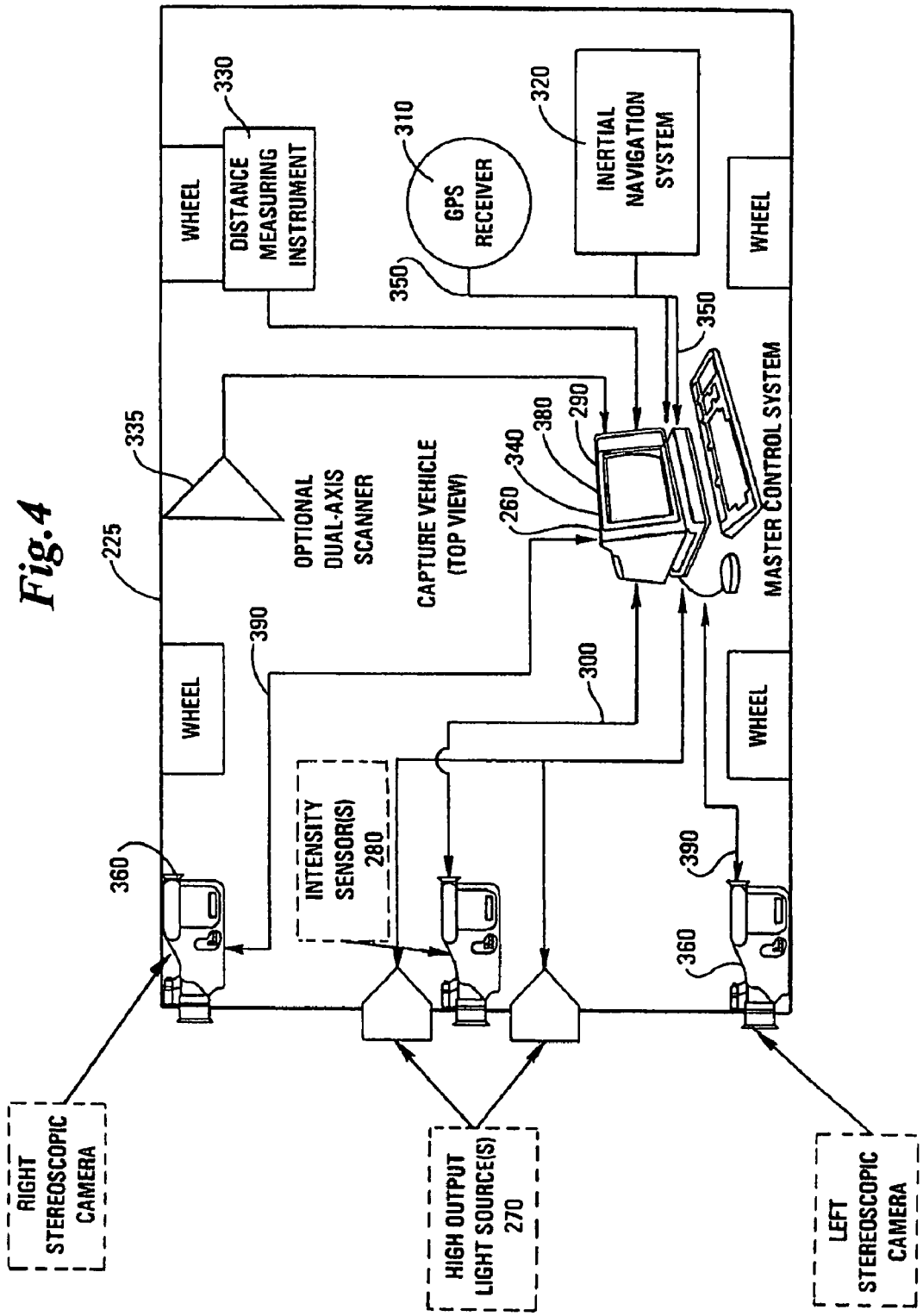
FIG. 4 depicts in diagram form, a preferred configuration of a sensor suite for use with a four-wheeled vehicle and the interconnections and couplings between the physical sub-components of a system designed according to the present invention.

FIG. 4 shows a typical configuration within a capture vehicle that is capable of producing data and imagery to create digital representations of objects of interest 460 and objects of interest retroreflectivity 466. The distance measuring instrument (DMI) 330, GPS receiver 310 and inertial navigation system (INS) 320 constitute the vehicle positioning system 240. Not all of these components are necessary to obtain the desired results, but better precision, and therefore more meaningful data, are produced if all three components are included.

The high output light source(s) 270 and light intensity sensor(s) 280 constitute the light intensity measurement system 230. These components make it possible to gather on-the-fly information for a desired highway 150 to allow the computation of object of interest retroreflectivity 466, as well as create a full three-dimensional sign $R_A$ profile 590 for those same objects of interest 460.

The stereoscopic cameras 360 constitute the digital imagery system 390 that allows for the creation of objects of interest 460 and their associated attributes 465 during post-processing. More than one set of stereoscopic cameras 360 can be employed, thus increasing the accuracy of positional measurements for objects of interest 460. Other, non-stereoscopic imaging systems could also be employed with little or no change to the vehicle positioning system 240 or to the light intensity measurement system 230.

FIG. 5 shows the top view of a four-lane divided highway 400 with a stop sign 190. The capture vehicle 225 is traveling in the proximate lane 410 to the stop sign 190 and makes intensity measurements 300 at capture events 430 while traveling the depicted route. The techniques described herein will allow a retroreflectivity value for this stop sign 190 to be computed for any point along the 4-lane divided highway 400, independent of whether the intensity measurement 300 was made at that point, and also independent of whether the capture vehicle 225 actually drove over that point.

It should be noted that intensity measurements 300 are made continuously while the capture vehicle 225 is in motion, thus requiring no prior knowledge of either the positions or the existence of signs.

FIG. 6 shows some typical reflected light intensity frames 420 as captured by the light intensity sensor 280 at various discrete locations along the roadway. These reflected light intensity frames 420 are the result of the high output light source 270 being energized (or flashed) while each reflected light intensity frame 420 is captured by one or more light intensity sensors 280. Since most of the objects in the scene are not reflective, and due to the high setting of the threshold range in the light intensity sensor(s) 280, the reflected light intensity frames 420 will actually show very few objects. For effective luminance results throughout a wide range of retroreflective materials, more than one light intensity sensor 280 may be required in order to get enough levels of gray within the active part of the visible spectrum. When multiple light intensity sensors 280 are required or used, they may each have different threshold ranges and each, thus, detect luminance values in different parts of the desired luminance ranges.

In order to compute retroreflectivity ($R_A$), one needs to know the luminance of the reflected energy. Luminance (expressed in candelas per square meter, or $cd/m^2$) will vary according to the intensity sensor characterization profile 275 of the light intensity sensor(s) 280 and the color of the material from which light is reflected.

Most roadway signs 190 contain text and/or symbols overlaid on a background. To ensure maximum visibility during day and night conditions, the colors of the foreground information (text and/or symbols) are chosen to have maximum day and night contrast with the background material. The techniques taught herein allow the retroreflectivity of roadway signs 190 to be determined for both foreground and background materials. Computing both the foreground 530 and background retroreflectivity 520 for each object of interest 460 allows us to ensure that the proper nighttime contrast is achieved for roadside assets. For example, a stop sign 190 with a red background and white lettering can provide good daytime contrast between the text and the sign background. But if these two materials display very similar retroreflectivity characteristics, their nighttime contrast will be minimal, thus rendering the sign ineffective during nighttime conditions.

Figure 7:
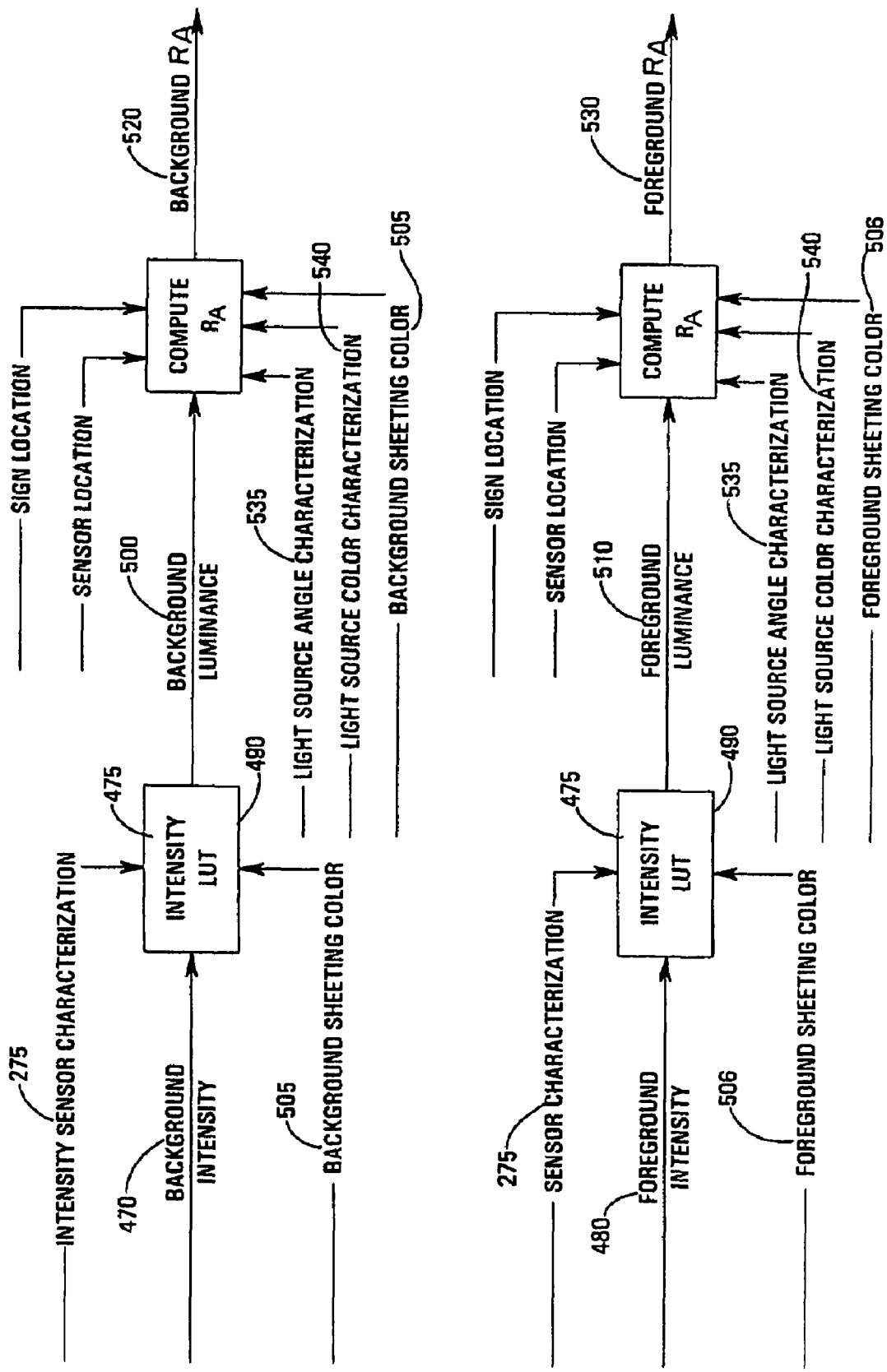
FIG. 7 depicts a flowchart showing the steps required to convert intensity measurements into foreground and background retroreflectivity for a single reflective asset.

FIG. 7 shows a block diagram of the steps required to transform intensity measurements 300 into foreground luminance values 510 and background luminance values 500. First, a black and white camera is preferably used as a light intensity sensor 280 to maximize the sensitivity of intensity measurements 300 (intensity will be determined from the gray value of the corresponding pixels). Think of an intensity measurement 300 as intensity values for N discrete points within the scene, where N corresponds to the number of pixels in the light intensity sensor's 280 array. For a light intensity sensor 280 that has a resolution of 640×480 pixels, there are 307,200 discrete intensity values for each intensity sensor measurement 300. Although the preferred embodiment utilizes an intensity sensor measurement 300 in the form of an array of discrete pixel intensity values, preferably a single pixel intensity value is selected and utilized for the automated determination of a corresponding retroreflectivity value. Alternatively, an average or other combination of a group of pixel intensity values could be utilized for the automated determination of a corresponding retroreflectivity value. Intensity values will vary according to the color of the reflected light, since not all colors of incoming light excite the light intensity sensor 280 pixels in the same way. By knowing the background or foreground color of the object of interest 460 along with the light intensity sensor's 280 ability to sense, or the light intensity sensor's 280 profile for a particular color, the intensity value 300 for a particular color can be converted into a luminance value. Light intensity sensor 280 characterization is essential for high precision computations since N photons of a given particular color (or wavelength) of light will represent a different gray value (intensity level) in the sensor than N photons of another color (or wavelength) of light. The look-up-table (LUT) 475 shown in FIG. 7 is a digital table stored in memory that uses the indexes of intensity (a single gray level value from the intensity measurement 300) and sheeting color to determine the luminance. The light intensity sensor characterization 275 is empirical information about the light intensity sensor 280 that is used to create the LUT 475. The same LUT 475 is used for computing foreground 510 and background luminance values 500.

The reader should note and appreciate that luminance is strictly a measure of the reflected light, while retroreflectivity (or $R_A$, expressed in candelas/lux/m²) is a measure of the reflected light with respect to the incident light for that object. FIG. 7 shows the information needed to accurately convert luminance to $R_A$: sensor location, object location, light source characterization, and color of reflective material. For less precise $R_A$ computations, a subset of the aforementioned characteristics can be utilized. For example, if a uniform light source (equal intensity throughout the scene), columnated light reflected from the surface of the object of interest 460, and a known distance 220 between the object of interest 460 and the light intensity sensor 280 are all assumed, then the sheeting color and luminance value may be used to determine a rough approximation (within 20%, for example) for $R_A$.

To obtain the highest quality $R_A$ calculations, all of the data shown in FIG. 7 should be utilized. The characterization of light source angle defines the amount of light emitted from the high output light source 270 throughout the source's field of view. Due to the limitations of lamp design and their associated reflectors, most semi-uniform light sources will have their greatest intensity at or near the normal vector for the light source. Since the high output light source(s) 270 are not aimed at objects of interest 460, the part of the incident light beam that is striking the object of interest 460 when the intensity measurement 300 is captured must be determined. Light source angle characterization is a process whereby empirical data from the light is modeled to establish the light intensity for numerous discrete vectors from the center of the light. When intensity values are determined for a discrete point in the scene (from the object's face surface 130), the light intensity sensor 280 location and heading, as well as the object of interest 460 location, are used to determine which light vector eliminating from the light source was responsible for the resulting intensity measurement. The characterization of light source angle therefore, is a look-up-table where an object of interest's 460 angular displacement from the normal vector 180 for the high output light source 270 is converted to a light intensity for the associated vector.

Since the beam from the high output light source 270 is diverging, objects of interest 460 farther from the origin of the light will receive less incident radiation than those objects of interest 460 closer to the light. The characterization of light source angle is constructed at a few discrete distances from the light. Simple geometry can be used to compute the incident radiation (using an interpolation method for an actual distance between two discrete distances in the characterization of light source angle) hitting the actual object of interest 460 based on the empirical data from the characterization of light source angle.

Figure 8:
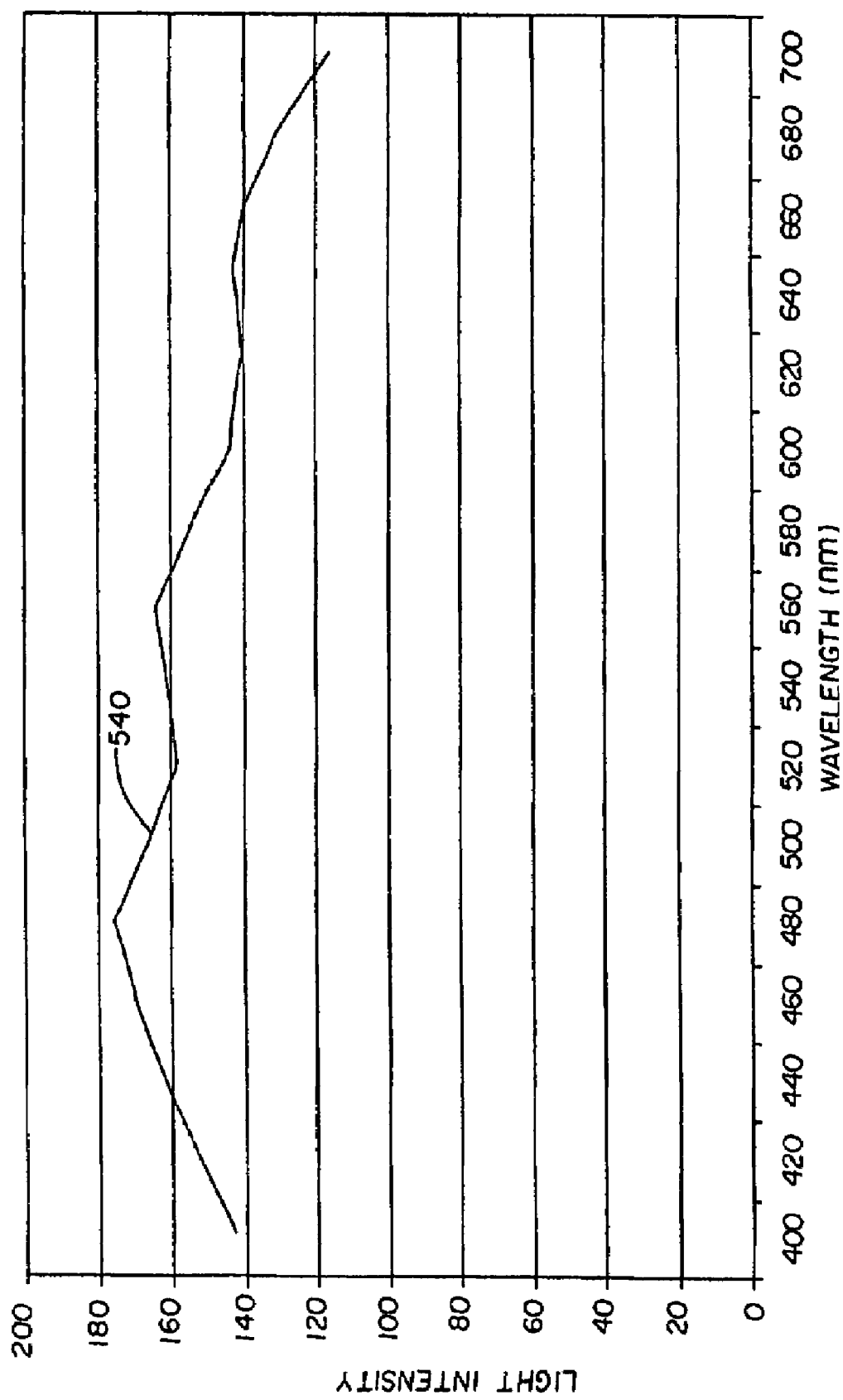
FIG. 8 depicts a typical light source intensity profile over the visible electromagnetic spectrum, which illustrates how different wavelengths of electromagnetic radiation possess different light intensities.

The preferred high output light source 270 is a uniform full-spectrum (visible spectrum) light. In practice, this light source will not emit the same intensity for all wavelengths of visible light. One variable of light source color characterization that should be considered is the output profile of the light throughout the visible spectrum. FIG. 8 shows a typical full-spectrum light source output profile. Note that the intensity in the blue area (400-500 nm) of the spectrum is stronger than in the red area (600-700 nm). This profile specifies the amount of light energy (number of photons) emitted for a given frequency. Since $R_A$ depends on the intensity of the incident light, the light source color characterization 540, light source angle characterization 535, background sheeting color 505 and foreground sheeting color 506 must be combined to determine how the background luminance value 500 and foreground luminance value 510 is converted to $R_A$ (i.e., what percent of the incident photons of the foreground/background color were reflected back to the sensor).

The divergence pattern for the light source may have different profiles for various portions of the visible spectrum. In practice, a separate light source angle characterization profile may be required for each possible foreground and background color of any given object of interest 460.

A preferred high output light source 270 is of the type set forth in the attached installation and operation guide entitled "StrobeGuard™ High Intensity Obstruction Lighting System, Model No. SG-60," manufactured by Honeywell, Inc. In order to create a useful three-dimensional sign $R_A$ profile 590 for an object of interest 460, intensity measurements 300 for frequent capture events 430 along a highway 150 while the capture vehicle 225 is in motion. For example, at vehicle speeds of 50 miles per hour, intensity measurements 300 should be taken at a rate of at least two per second. The StrobeGuard™ SG-60 model has a recharge time of about 1.5 seconds between successive flash events. As a result, one SG-60 light will not provide enough flash events per second to allow an adequate number of intensity measurements 300. In order to meet the requirements of two flash events per second for a capture vehicle 225 traveling at 50 miles per hour, three of the StrobeGuard™ SG-60 units would need to be fired in a synchronized, round-robin pattern to obtain enough trigger events.

The light intensity measurement system 230 described herein attempts to remove observation angle 100 as an $R_A$ variable. This is done by keeping the offset between the high output light source(s) 270 and light intensity sensor(s) 280 as low as possible. Once a simulated roadway 580 is created, observation angles 100 can be varied within the three-dimensional display software or within the virtual drive-through software to show their effects on the $R_A$ for the simulated roadway 580 and any as-placed sign 190.

As mentioned previously, a $R_A$ map of a simulated roadway 580 can be computed, even though the intensity was not measured at every point and even though the capture vehicle 225 did not drive over every point. First, it is critical that the geometry of $R_A$ is understood. Reflective materials like sign sheeting are designed to project near-columnated light back toward the light source. If a perfectly columnated light being reflected from the object of interest 460 being measured and a zero observation angle are assumed, the $R_A$ values for all discrete locations along a ray projected from the object will be identical.

FIG. 9 shows how to compute $R_A$ for any discrete location along a 4-lane divided highway 400. The $R_A$ value for the desired point will be based on the $R_A$ value that lies along the pathway traveled by the data acquisition vehicle 225. To compute this "reference $R_A$ value" (the $R_A$ value for a discrete location on or along a vehicle path), an undetermined retroreflectivity ray 570 is drawn from the desired location to the face of the reflective asset. The discrete location where the undetermined retroreflectivity ray 570 intersects the vehicle path will be used as the reference $R_A$ value. Since the discrete location on the vehicle path will always lie between two measured locations where intensity measurements 300 were made, the reference $R_A$ value is computed by interpolating the two closest (in distance) $R_A$ values along the vehicle path. As used herein, interpolate has the usual and typical meaning. It will be understood that interpolation consistent with the present invention can involve interpolation followed by extrapolation and shall also include such other special mathematical expressions used or created to account for border effects and effects at the lateral periphery and at the furthest distance where $R_A$ may be reliably determined by application of the teaching of this disclosure.

If a perfectly columnated light is assumed, the value of $R_A$ at the desired point will be the same as the reference $R_A$ value. In practice, all sign 190 sheeting materials will have some beam divergence for reflected light. This beam divergence information can be used to adjust the computed $R_A$ value up (or down) from the reference $R_A$ value for discrete locations closer to (or farther from) the object's face surface 130.

While knowing the normal vector 180 to a sign 190 face is not required, there are some advantages for planning and maintenance purposes that make the information useful. Several ways to compute the normal vector 180 for a sign 190 exist. First of all, the "assumption" method requires that the normal vector 180 from the surface of the sign 190 is assumed to be parallel to the capture vehicle pathway 410 at the nearest location of the capture vehicle pathway 410 to the sign 190. Second, a scanning laser operating in conjunction with an optical sensor and having a common field of view may be used to more precisely resolve the normal vector 180 from the object's face surface 130. Third, stereoscopic cameras 360 may be employed in a useful, albeit very imprecise, manner of determining the normal vector 180. Fourth, the assumption method and stereo imaging method may be combined whereby the normal vector 180 is assumed to lie parallel to the vehicle pathway 410 unless the stereo imaging output renders the assumption false.

Of the methods listed above, the highest precision measuring systems for determining the normal vector 180 consists of a scanned laser and associated optical sensor. This combination yields relative distance measurements between the capture vehicle 225 and the object's face surface 130 that are more precise than optical measurements with cameras. A laser scanner attached to the capture vehicle 225 and directed toward a roadside scene populated with retroreflective signs 130 generates a series of reflection points to the optical sensor that appear as a horizontal segment of points. The optical sensor must be fast enough (i.e., have adequate data acquisition rates) to capture at least several individual discrete measurements across the object's face surface 130 (or of any other reflective asset). In general, two types of laser scanners are suitable to be utilized according to the present invention; namely, single-axis scanners and dual-axis scanners. A preferred sensor is of the type set forth in the proposal entitled, "*Holometrics* 3*D Vision Technology*," as referenced in the previously identified provisional patent application.

Since most all types of roadside signs 190 to be measured are disposed at various elevations relative to the highway 150 and the capture vehicle 225, a single-axis laser scanner cannot be mounted such that the scanning laser beam covers only a single elevation or constant height relative to the highway 150 and the capture vehicle 225. Rather, the inventors hereof suggest that use of a single-axis type laser scanner must either be mounted high on the capture vehicle 225 with a downward facing trajectory, or be mounted low on the capture vehicle 225 with an upward facing scanning trajectory. These two mounting schemes for a single-axis laser scanner help ensure the lateral scan will intersect with virtually every object face surface 130 of all signs 190 or other objects of interest 460 present in a roadside scene regardless of the elevation or height or such signs relative to the roadway or to the moving platform.

Dual-axis laser scanners 335 circumvent the varying sign height problem inherently encountered if a single-axis laser scanner is employed as the source of integrated energy when practicing the teaching of the present invention. A dual-axis laser scanner 335 operates by continuously moving the scanning beam scan up and down at a relatively slow rate while sweeping the laser beam laterally from side to side across the field of view at a relatively more rapid rate.

In order to obtain the normal vector 180 for a sign 190 as taught hereunder, only a select horizontal series of discrete locations across the object's face surface 130 needs to be sensed by the high-speed optical sensor. For each point in the horizontal series of discrete locations recorded for a given sign 190 due to the incident radiation provided by the scanning laser, as sensed by the high speed optical sensor, the precise direction of the incident laser is recorded, thus allowing both distance and direction of the measured point to be determined.

Either of the scanning methods produces a massive number of sensed discrete locations representing discrete reflections of the incident laser radiation and each must be processed in order to correlate each of the sensed discrete locations with the object's face surface 130. Once the lateral series of discrete locations for a sign 190 is determined, simple triangulation methods are used to combine: (i) the vehicle location, (ii) vehicle heading vector, and (iii) scanned sign point to ultimately determine the normal vector 180 for the object's face surface 130.

As stated earlier, knowing the sign's 190 normal vector 180 can expand the utilization of the present invention. The retroreflective properties of sign 190 sheeting materials are typically symmetrical about the vertical axis of the object's face surface 130. Because of this symmetry, $R_A$ values (either computed or extrapolated/interpolated values) will be identical for rays that are symmetrical about the vertical axis.

FIG. 10 shows how the sign's 190 normal vector 180 can be used to extrapolate more $R_A$ points. The $R_A$ value for Point B is the same as the $R_A$ value for Point A since their angle relative to the normal vector 180 is the same and since their distance from the sign 190 is the same. If Point B has the same relative angle (from the sign's 190 normal vector 180) as Point A, but lies closer to (or farther from) the object's face surface 130, the sign 190 material's beam divergence profile can be used to adjust the $R_A$ value for Point B up (or down) from the value obtained for Point A.

While the image capture system 250 described herein can be used for locating objects of interest 460, it can also be used for mapping purposes. By creating representations of roadway edges and lane dividers, a very precise map can be created from the same digital imagery used for object of interest 460 creation. This mapping feature of the image capture system 250 will be a key component in the three-dimensional sign $R_A$ profile 590 mapping for signs and the virtual drive through, both to be discussed later.

The image capture system 250 and light intensity measurement system 230 are preferably free running, with measurements being made periodically during capture vehicle 225 operation. There is no requirement that these two systems be synchronized. In fact, these systems could operate in completely different capture vehicles 225, if necessary. When both systems are contained within the same capture vehicle 225, the only constraint for simultaneous operation is placed on the image capture system 250. Because of the intensity of the high output light source 270 in the light intensity measurement system 230, it is preferred that the image capture system 250 not capture frames at the same instant that the high output light source 270 is triggered. If images are actually captured while the high output light source 270 is triggered, their positional results would still be valid, but the colors displayed would be inaccurate because of the high output light being directed toward the (typically lower-thresholded) stereoscopic cameras 360.

One skilled in the art could completely eliminate any need for the image capture system 250 to know the firing events of the light intensity measurement system 230 by choosing sampling rates for the two systems that do not share any harmonic frequencies. On the rare occasions when the image capture system 250 captures images while the high output light source 270 is energized (or flashed), the skilled implementer could use time stamps to determine when this system simultaneity occurred and discard the imaging frames.

Producing a simulated roadway 580 map is an essential part of creating a three-dimensional sign $R_A$ profile 590 for a given vehicle 140 pathway. All maps of a highway 150 will contain some degree of error. Even survey-grade maps, which are expensive to create and cumbersome to build, may have errors of a few centimeters to a few inches or more. Maps created via other methods, such as those made from data gathered from capture vehicles 225, could have errors ranging from a few centimeters to several meters.

In practice, the simulated roadway 580 map created from the inventive image capture system 250 as disposed in or on a capture vehicle 225 and as otherwise described herein will be of higher value for the three-dimensional sign $R_A$ profile 590 than a survey-grade map. Even though the absolute errors may be greater in a two-dimensional or three-dimensional map created using the image capture system 250 of the present invention, they will be very small relative to the actual location of individual objects of interest 460 and also very small with respect to the discrete locations where the $R_A$ measurements—both computed and extrapolated or interpolated values—were made. The same systematic location errors may permeate all data points, but the relative accuracy will be high. Since $R_A$ is very dependent on the geometry of the objects of interest 460 and the magnitude and direction of the light incident thereon, a high degree of relative accuracy in creating a simulated roadway 580 base map of such all inventoried objects of interest 460.

Figure 11:
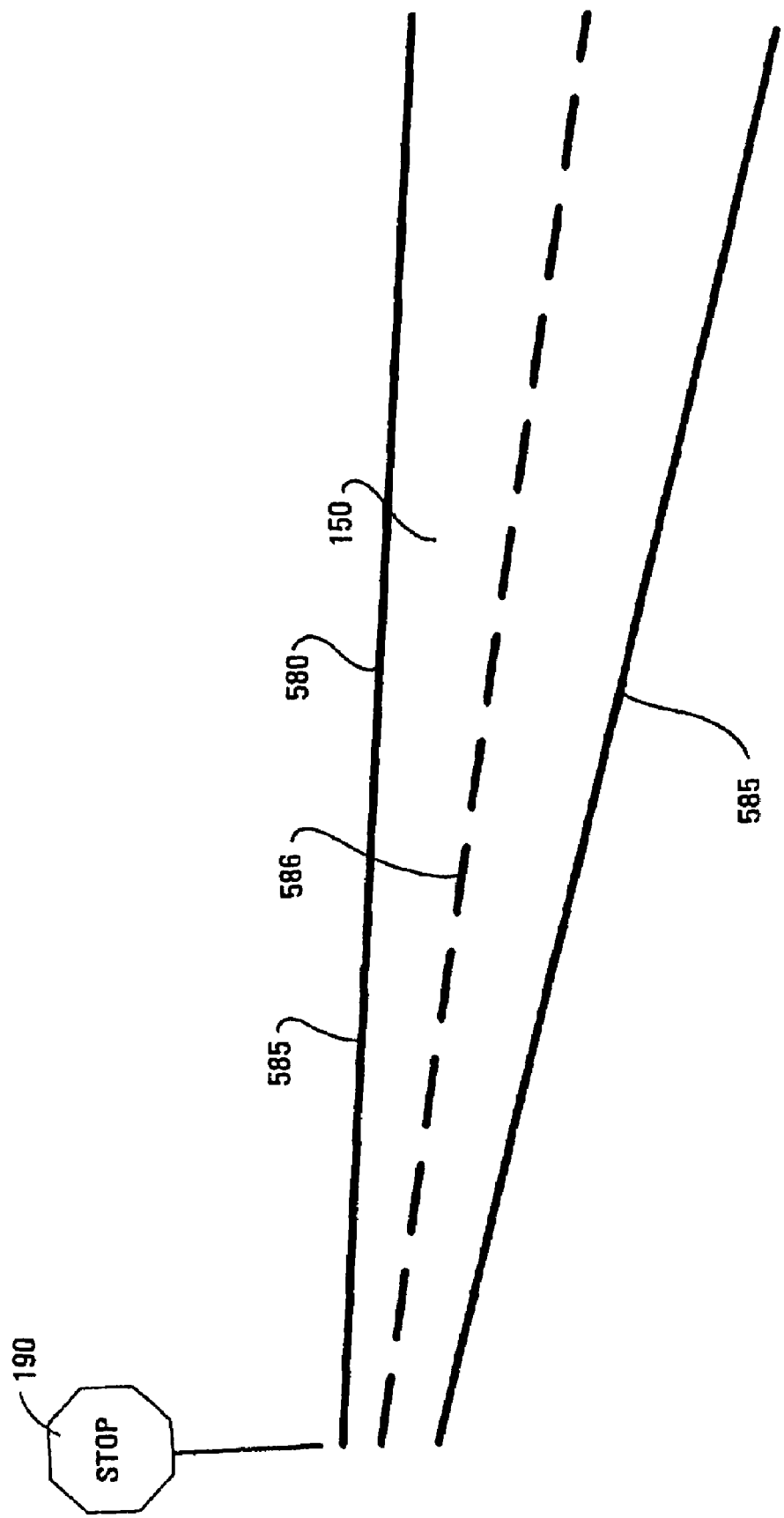
FIG. 11 depicts a typical map of roadway edges and lane dividers created from the imaging system on-board the moving platform or data acquisition vehicle.

FIG. 11 shows another typical highway 150 that was driven by a capture vehicle 225 fabricated according to the teaching of the present invention. Data from this capture vehicle's 225 image capture system 250 was used to create the simulated roadway 580 map including roadway edges 585 and lane dividers 586. The same image capture system 250 data was used to locate the sign 190, measure its size, and determine other attributes. This same capture vehicle 225 also gathered intensity measurements 300 for the highway 150 shown in FIG. 11. The intensity measurements 300, along with the sign 190 location and sign 190 colors, were used to create $R_A$ values for the discrete locations within the lane of travel. A "point cloud" of data points was then calculated to create a full three-dimensional sign $R_A$ profile 590 for this particular sign 190 along the entire highway 150.

Figure 12:
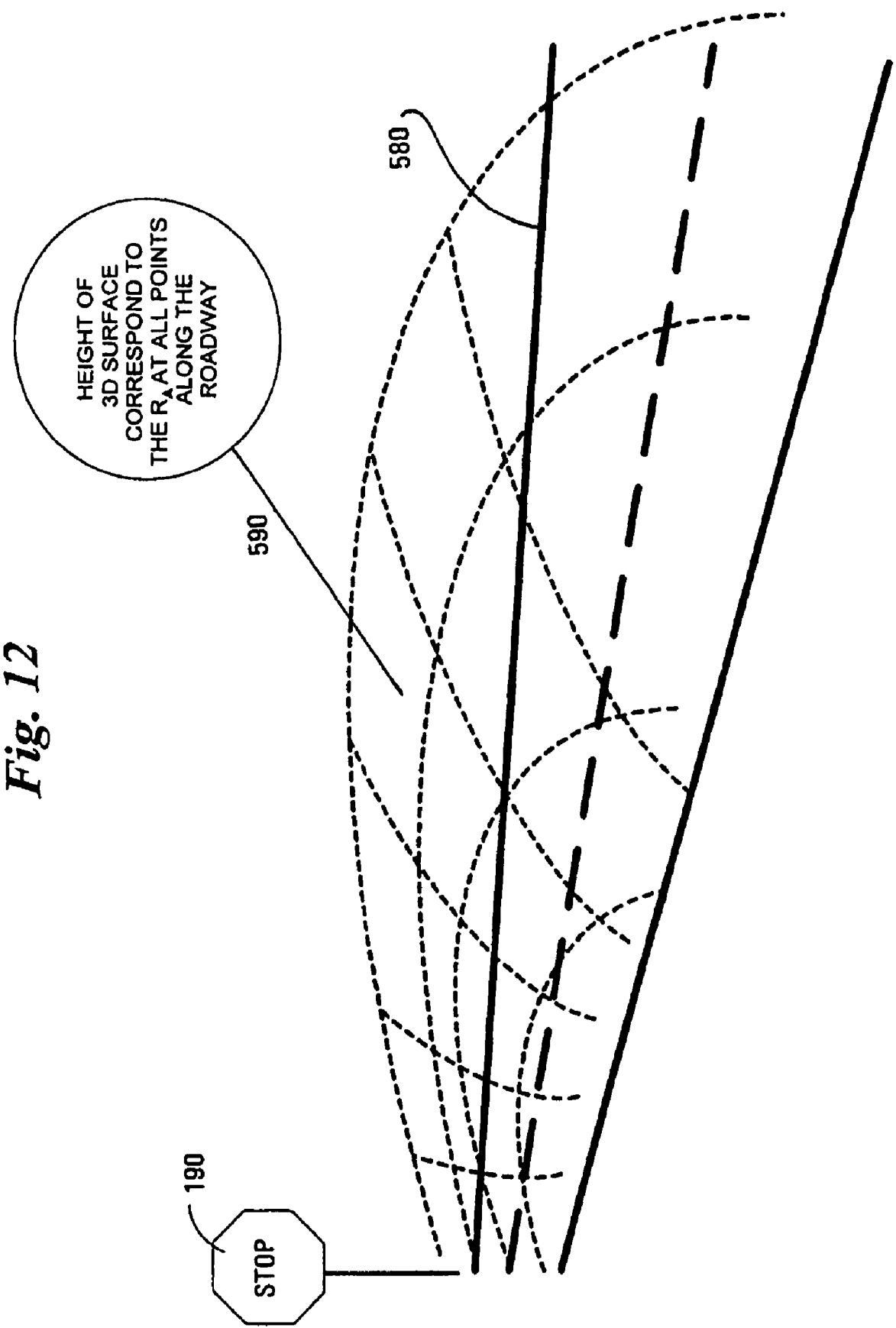
FIG. 12 is an elevational side view depicting a three-dimensional retroreflectivity profile for a stop sign created from the moving platform wherein the height of the three-dimensional surface at each point represents the magnitude of the retroreflectivity of the sign at that point.

FIG. 12 shows a three-dimensional representation of the point cloud of $R_A$ values for the sign 190 along the highway 150. The height of the three-dimensional sign profile 590 at each point represents that sign's 190 $R_A$ value at that point. Planning and maintenance departments within transportation agencies will see the obvious benefits in graphically representing a sign's 190 $R_A$ performance over the surface of a highway 150. Along with understanding a sign's 190 current performance, these agencies can use the $R_A$ profile software to understand how changes to a sign 190 can affect its performance along a given highway 150.

Figure 13:
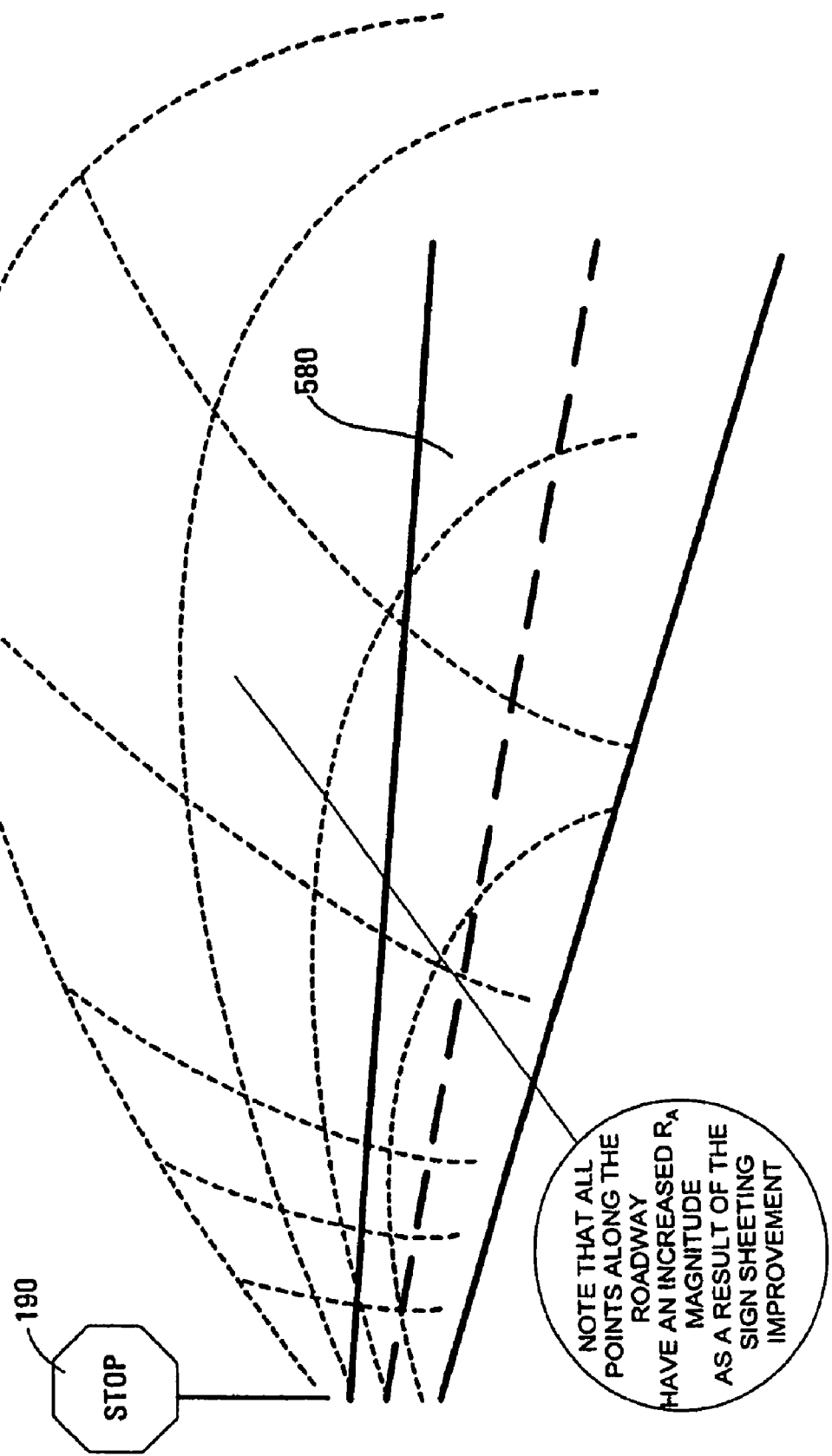
FIG. 13 is an elevational side view depicting a modified three-dimensional retroreflectivity profile resulting from a change to the sign sheeting type that produces higher intensity visible radiation reflected from the stop sign.

FIG. 13 shows the impact of one possible variable on the sign's 190 three-dimensional sign $R_A$ profile 590. If, for example, the measured sign 190 utilized a medium performance sheeting type, the display software can show the impact of changing the sheeting type for this sign 190. The display software has performance curves for the desired sheeting type and computes the new three-dimensional sign $R_A$ profile 590 for this sign 190 using its current location, size, and facing direction.

Figure 14:
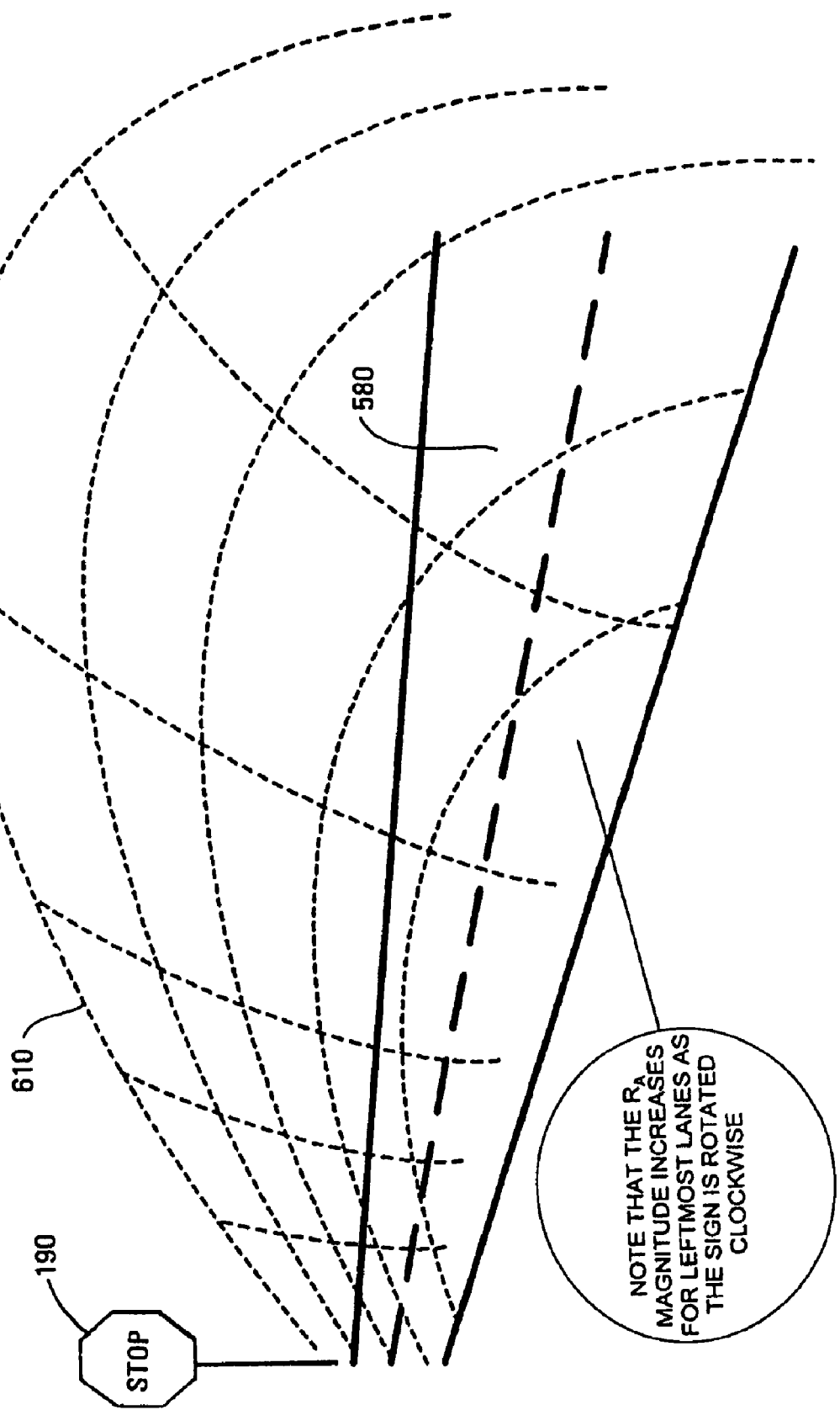
FIG. 14 is an elevational view depicting a modified three-dimensional retroreflectivity profile resulting from a change in the angle of a given reflective asset with respect to the roadway.

FIG. 14 shows how changing the sign 190 angle (which changes the entrance angle 160) would impact the sign's 190 three-dimensional sign $R_A$ profile 590. Even though a system fabricated, according to the present invention, may not have direct measurement or other data regarding the exact angle entrance angle 160, one may use the computed $R_A$ data points to create a three-dimensional sign $R_A$ profile 590 and rotate the three-dimensional sign $R_A$ profile 590 as specified by the user any arbitrary degree or fraction thereof. This feature assists traffic sign maintenance department personnel in "tuning $R_A$ to the highway 150" for all or any portion of such object's of interest 460 and/or each roadside sign 190 (i.e., various entrance angles 160 from different segments of a vehicle pathway yield different results).

If a sign 190 on the right hand side of the road is rotated on an axis perpendicular to a vehicle pathway one may not have enough computed $R_A$ points from the capture vehicle 225 given the track or path of such vehicle with which to compute the complete three-dimensional sign $R_A$ profile 590 for the entire highway 150 surface. However, if we know the normal vector 180 for the sign 190 (via any of the various methods described herein), one may use the typical horizontal symmetry of sign 190 sheeting materials to create the rest of the three-dimensional sign $R_A$ profile 590.

Figure 15:
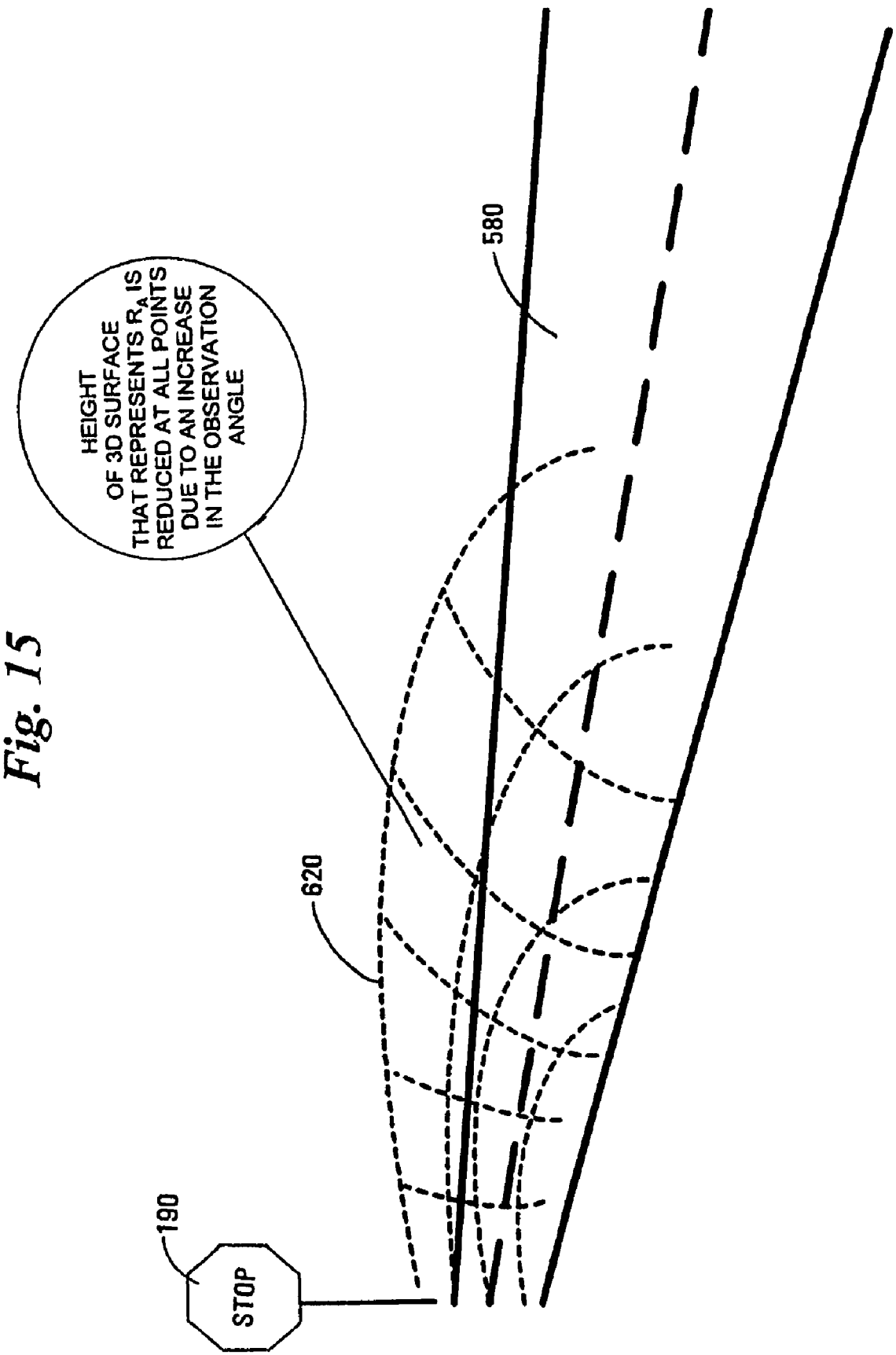
FIG. 15 depicts the modified three-dimensional retroreflectivity profile resulting from a change in the observation angle.

As mentioned earlier, observation angle 100 is a key determinant for sign 190 $R_A$ behavior. The light intensity measurement system 230 contained herein attempts to eliminate this variable by placing the high output light source(s) 270 and light intensity sensor 280 very close to one another. Planning departments can change observation angles 100 within the three-dimensional sign $R_A$ profile 590 software to understand its impact on sign 190 performance. Since the three-dimensional sign $R_A$ profile 590 software knows the as-measured sign 190 sheeting type and has available an $R_A$ performance profile (preferably embedded in a look up table of all popular or required sheeting types and/or as stored in memory, or dynamically generated for use in practicing the present invention), a new three-dimensional sign $R_A$ profile 590 can be generated for the newly-desired observation angle 100. FIG. 15 shows the observation angle simulation 620 for the sign 190 along the sample highway 150 when the observation angle 100 is changed from its present value to a higher value.

The aforementioned three-dimensional sign $R_A$ profile 590 is one way of utilizing the $R_A$ data to assess the object's of interest 460 performance. A "virtual drive-through" is another method of utilizing the computed $R_A$ data. Virtual drive-throughs are a popular tool used by transportation and planning departments. These drive-throughs consist of creating a three-dimensional volumetric model of a particular highway 150. Users of virtual drive-through applications can then move the view point along the highway 150 to understand what a driver (in a passenger vehicle, for example) would see as they traversed the selected highway 150. These drive-throughs, however, are usually modeled using information from the daytime scene.

Nighttime drive-throughs, on the other hand, can provide useful information beyond what can be learned from daytime drive-throughs. To properly represent nighttime drive-throughs, accurate information must be integrated regarding the nighttime performance of the objects of interest 460. As a result of the creation of an three-dimensional sign $R_A$ profile 590 for each object of interest 460, these objects of interest 460 assets can be placed in the virtual drive-through at their precise locations along the highway 150 (or on the highway 150 in the case of pavement markings 630). Utilizing nighttime asset performance in a virtual drive-through can highlight design or implementation problems that are not apparent with daytime virtual drive-throughs. Assessment of nighttime accidents can be significantly enhanced by using nighttime asset performance information in virtual drive-throughs.

Although the use of the three-dimensional sign $R_A$ profile 590 has been described with respect to $R_A$ values as determined by measurement of light intensity, it will be understood that the software for manipulating the three-dimensional sign $R_A$ profile 590 and the virtual drive-through can work equally as well in other modes where known data values are provided for some or all of the to $R_A$ values. For example, planning departments could insert $R_A$ values for known sheeting types of planned signs along a roadway in order to conduct a night time virtual drive through utilizing the software in accordance with the present invention to manipulate the location and placement of such signs to achieve better visibility.

Reflective pavement markings 630 display similar properties to objects of interest 460 (and other reflective objects), but the determination of pavement marking 630 retroreflectivity requires some extra constraints. Pavement marking 630 retroreflectivity is expressed in millicandelas per square meter per lux (mcd/m$^2$/lux) and is designated $R_L$. Along with observation angle 100 and entrance angle 160, the lateral distance 220 between the light source 110 and the pavement markings 630 must also be known. FIG. 16 shows the $R_L$ geometry for a typical passenger vehicle 140.

Studies have shown that there is no correlation between pavement marking 630 retroreflectivity ($R_L$) values with different geometries. Because of this lack of correlation, agreed-upon geometries must be utilized when measuring intensity and reporting $R_L$. When measuring intensity and computing $R_A$ the present invention attempts to dramatically reduce (essentially eliminate) observation angle 100 with the high output light source 270 and light intensity sensor 280 placement. When measuring intensity for computing $R_L$, it is preferable to position the high output light source 270 and the light intensity sensor 280 such that the agreed-upon geometry is met for the desired measurement distance. At the time of this disclosure, both the European Committee for Normalization and the American Society for Testing and Materials (ASTM) have standardized on the same $R_L$ geometry of 1.05 degree observation angle 100, 88.76 degree entrance angle 160, and 30 meter measurement distance 220.

The intensity of light reflected from pavement markings 630 will be less than that of signs 190. As a result, another light intensity sensor 280 may be needed for the determination of $R_L$. Therefore, there are two reasons for requiring a different light intensity sensor 280 for determining $R_A$ and $R_L$—the range of intensities and the placement of the light intensity sensor 280. However, the same high output light source(s) 270 can be used for determining $R_A$ and $R_L$.

The present invention has been described with respect to particular illustrative embodiments. It is to be understood that the invention is not limited to the above-described embodiments and modifications thereto, and that various changes and modifications may be made by those of ordinary skill in the art without departing from the spirit and scope of the appended claims.

What is claimed:

1. A method of automated determination of retroreflectivity values for reflective surfaces comprising:
    strobing a light source to illuminate an area that includes at least one reflective surface without targeting the light source on a particular reflective surface;
    collecting a plurality of light intensity measurements with at least one intensity sensor directed to cover a field of view which includes at least a portion of the area illuminated by the light source; and
    using a computer processing system to:
        identify a portion of at least one light intensity measurement associated with one of the at least one reflective surfaces; and
        analyze the portion of the at least one light intensity measurement to determine at least one retroreflectivity value for that reflective surface.

* * * * *

UNITED STATES PATENT AND TRADEMARK OFFICE
CERTIFICATE OF CORRECTION

PATENT NO. : 7,411,681 B2  Page 1 of 1
APPLICATION NO. : 11/702421
DATED : August 12, 2008
INVENTOR(S) : Retterath et al.

It is certified that error appears in the above-identified patent and that said Letters Patent is hereby corrected as shown below:

Title page, Item (63), line 6, after "Pat. No. 6,674,878" please insert --, which claims priority to U.S. Provisional Application No. 60/296,596, filed Jun. 07, 2001--.

Signed and Sealed this
Fourteenth Day of August, 2012

David J. Kappos
*Director of the United States Patent and Trademark Office*